(12) United States Patent
Nicholls et al.

(10) Patent No.: US 9,804,091 B2
(45) Date of Patent: Oct. 31, 2017

(54) ASSAY TEST CARD

(71) Applicant: L3 TECHNOLOGY LIMITED, Ledbury (GB)

(72) Inventors: Anthony Nicholls, Ledbury (GB); Laura Garcia, Ledbury (GB); Mark Hudson, Ledbury (GB); Gareth Jones, Ledbury (GB); David Clarke, Ledbury (GB)

(73) Assignee: L3 Technology Limited, Ledbury (GB)

( * ) Notice: Subject to any disclaimer, the term of this patent is extended or adjusted under 35 U.S.C. 154(b) by 0 days.

(21) Appl. No.: 13/948,270

(22) Filed: Jul. 23, 2013

(65) Prior Publication Data

US 2013/0323764 A1    Dec. 5, 2013

Related U.S. Application Data

(63) Continuation of application No. 13/054,211, filed as application No. PCT/GB2009/050860 on Jul. 15, 2009, now abandoned.

(30) Foreign Application Priority Data

Jul. 15, 2008 (GB) .................................. 0812907.4
May 28, 2009 (GB) .................................. 0909130.7

(51) Int. Cl.
*G01N 21/75* (2006.01)
*G01N 21/64* (2006.01)
(Continued)

(52) U.S. Cl.
CPC ......... *G01N 21/64* (2013.01); *B01F 13/0071* (2013.01); *B01F 13/0084* (2013.01);
(Continued)

(58) Field of Classification Search
CPC ....... B01L 2300/0816; B01L 3/502715; B01L 2300/0887; B01L 2300/165;
(Continued)

(56) References Cited

U.S. PATENT DOCUMENTS 4,963,498 A   10/1990 Hillman et al.
6,027,890 A    2/2000 Ness et al.
(Continued)

FOREIGN PATENT DOCUMENTS

EP    1712919     10/2006
GB    2436616 A   10/2007
(Continued)

OTHER PUBLICATIONS

International Search Report, PCT/GB2009/050860, dated Jan. 21, 2010.
(Continued)

*Primary Examiner* — Dennis M White
(74) *Attorney, Agent, or Firm* — Klauber & Jackson LLC

(57) ABSTRACT

The present invention relates to the use of surfaces that exhibit different surface energies wherein the difference in surface energies is configured to disrupt capillary laminar flow of a fluid travelling between the two surfaces. The invention further relates to the use of such surfaces in assay methods including a device utilising same.

18 Claims, 7 Drawing Sheets

(51) Int. Cl.
*B01F 13/00* (2006.01)
*B01L 3/00* (2006.01)
*G01N 33/92* (2006.01)

(52) U.S. Cl.
CPC ........ *B01L 3/502769* (2013.01); *G01N 33/92* (2013.01); *B01L 2300/161* (2013.01); *B01L 2400/0406* (2013.01); *B01L 2400/088* (2013.01); *Y02P 20/582* (2015.11)

(58) Field of Classification Search
CPC .......... B01L 3/502792; B01L 2200/04; B01L 2300/0825; B01L 2300/0829; B01L 2200/0642; B01L 2200/0647; B01L 3/502769; B01L 2400/0406; B01L 2400/088; B01L 2300/161; G01N 2035/00326; G01N 21/64; G01N 33/92; G01N 2021/0346; G01N 21/6428; G01N 33/54366; G01N 2015/0288; G01N 21/05; G01N 33/5302; G01N 33/54386; G01N 33/4915; G01N 35/1095; B01F 13/0071; B01F 13/0084; Y02P 20/582
See application file for complete search history.

(56) References Cited

U.S. PATENT DOCUMENTS

| | | | |
|---|---|---|---|
| 6,207,000 B1 | 3/2001 | Schwobel et al. | |
| 6,485,982 B1 | 11/2002 | Charlton | |
| 7,829,023 B2 | 11/2010 | Burke et al. | |
| 2004/0028566 A1 | 2/2004 | Ko et al. | |
| 2005/0041525 A1* | 2/2005 | Pugia .................. | B01F 5/0644 366/341 |
| 2005/0048561 A1 | 3/2005 | Fulwyler et al. | |
| 2008/0314745 A1 | 12/2008 | Neubert et al. | |

FOREIGN PATENT DOCUMENTS

| | | |
|---|---|---|
| JP | 2007286069 A | 11/2007 |
| WO | 9005182 | 5/1990 |
| WO | 9114773 | 10/1991 |
| WO | 9324231 | 12/1993 |
| WO | 98/39645 A1 | 7/1998 |
| WO | 99/58245 A1 | 11/1999 |
| WO | 0102093 | 1/2001 |
| WO | 0174242 | 10/2001 |
| WO | 02085185 | 10/2002 |
| WO | 03/072227 A1 | 9/2003 |
| WO | 2004113901 | 12/2004 |
| WO | 2006/061026 A2 | 6/2006 |
| WO | 2006061646 | 6/2006 |
| WO | 2010/070461 A1 | 6/2010 |

OTHER PUBLICATIONS

Hönes et al., "The technology behind glucose meters: test strips", Diabetes Technology & Therapeutics, 2008, 10:S-10 to S-26.
Bi et al. "Deposition of PEG onto PMMA microchannel surface to minimize nonspecific adsorption", Lap Chip, 2006, 6:769-775.
Steigert et al., "Rapid prototyping of microfluidic chips in COC", J. Micromech. Microeng, 2007, 17:333-341.
Asthana et al., "Multifunctional superhydrophobic polymer/carbon nanocomposites: graphene, carbon nanotubes, or carbon black?", ACS Applied Materials & Interfaces, 2014, 6:8859-8867.
Iwata et al., "Design and synthesis of amphipathic 310-helical peptides and their interactions with phospholipid bilayers and ion channel formation", J Biol Chem, 1994, 269:4928-33.
Negrete et al., "Deciphering the structural code for proteins: Helical propensities in domain classes and statistical multiresidue information in α-helices", Protein Science, 1998, 7;1368-1379.
Neuman et al., "Surface and colloid science—experimental methods", Plenum Press, 1979, II:63-70.
Curry et al., "Crystal structure of human serum albumin complexed with fatty acid reveals an asymmetric distribution of binding sites", Nature Structural Biology, 1998, 5:827-835.
Grell et al., "Protein design and folding: template trapping of self-assembled helical bundles", Journal of Peptide Science, 2001, 7:146-151.
Chen et al., "Determination of stereochemistry stability coefficients of amino acid side-chains in an amphipathic α-helix", Journal Peptide Research, 2002, 59:18-33.
Cornut et al., "The amphipathic α-helix concept—Application to the de novo design of ideally amphipathic Leu, Lys peptides with hemolytic activity higher than that of melittin", FEBS Letters, 1994, 349:29-33.
Package of an ACCU-CHEK Aviva diabetes monitoring kit, Roche, 2005.
Package of an ACCU-CHEK Aviva test strips, Roche, 2009.
Adhesives Research, Inc., "Certified Test Report", 2007.
Dietz, "Contact angle study", dated Jan. 8, 2009.

* cited by examiner where $\gamma_{SG}$ = Interfacial tension between the solid and gas
$\gamma_{SL}$ = Interfacial tension between the solid and liquid
$\gamma_{LG}$ = Interfacial tension between the liquid and gas
$\varnothing_c$ = Contact angle

ASSAY TEST CARD

CROSS-REFERENCE TO RELATED APPLICATIONS

The present application is a continuation of U.S. patent application Ser. No. 13/054,211, which is a national stage application of international patent application number PCT/GB2009/050860, which claims priority both from UK patent application number 0812907.4 and UK patent application number 0909130.7.

FIELD OF THE INVENTION

The present invention relates generally to the field of disposable assay test devices, particularly for use in point-of-care assays. The invention further relates to the use of such devices, including kits comprising such devices, to facilitate the accurate measurement of the levels of various lipoproteins in the blood. Test kits may comprise one or more assay test devices and optionally include instructional leaflets, lancet devices, antiseptic alcohol swabs or adhesive bandages.

BACKGROUND TO THE INVENTION

Several publications and patent documents are referenced in this application in order to describe more fully the state of the art to which this invention pertains. The disclosure of each of these publications is incorporated herein by reference.

Lateral flow assay devices and methods are known in the art. Previously such devices have been developed to test samples that are easily available in large quantities. Generally such devices comprise a lateral flow matrix, such as a nitrocellulose matrix for example, to which a fluid sample is applied. Fluid within the sample travels along the matrix and one or more analytes within the sample react with reagents contained within the lateral flow matrix. Typically at least one of these reagents is immobilised within the matrix allowing any reaction with the analytes to be detected at a specific area of the matrix, for example, by visual inspection.

When the test sample is blood, or a component of blood, collection of a large sample is not always possible or convenient, for example at a point-of-care such as a pharmacy or a doctor's surgery. In addition, lateral flow devices are generally unsuitable for small fluid samples, such as for analysis of 'finger prick' volumes of blood. In this case the membrane may dry before the assay is completed or there may be insufficient fluid to travel the length of the test device before measurement is possible. Also, as the scale of devices in which fluids are manipulated is decreased, there exists the significant disadvantage that there is a tendency for such fluids to maintain a stable laminar flow. This makes efficient mixing of liquids and, for example, reagents difficult limiting the extent to which assay devices may be successfully reduced in scale without increasing the complexity of the device. FIG. 1 provides examples from the art of existing, complex, assay devices.

As such, a need currently exists for simple and efficient devices that allow rapid testing whilst enabling lower or smaller volumes of a sample to be analysed. One area where such devices would be useful is in the field of cholesterol and blood lipid testing.

SUMMARY OF THE INVENTION in a first aspect the invention provides an assay device comprising two at least partially opposing surfaces that exhibit different surface energies wherein the difference in surface energies is configured to disrupt capillary laminar flow of a fluid travelling between the two surfaces.

When a liquid is placed onto a surface, the degree to which it spreads across the surface is determined by surface tension. On a hydrophilic surface, liquid is attracted to the surface and spreads into a thin film. On a hydrophobic surface a liquid will spread less and may 'bead'. Surface energy is generally closely linked with surface hydrophobicity/hydrophilicity. Whereas surface energy describes interactions with a range of materials, generally surface hydrophobicity describes these interactions with water only. Because water has a huge capacity for bonding, a material of high surface energy (i.e. high bonding potential) can enter into more interactions with water and consequently will be more hydrophilic. Therefore hydrophobicity generally decreases as surface energy increases. Hydrophilic surfaces such as glass therefore have high surface energies, whereas hydrophobic surfaces such as PTFE or polystyrene have low surface energies.

A suitable measure for assessing the hydrophilic/hydrophobic nature of a substance, and therefore its surface energy, is the contact angle (ø) of a liquid on the respective surface.

The contact angle is the angle formed between a line tangential to the surface of a liquid droplet and the plane of the surface on which the droplet is formed. A hydrophobic surface creates less interfacial tension with a liquid droplet creating a greater contact angle. The measurement of contact angles is well known in the art, for example, contact angles may be determined as described in Robert J. Good and Robert J. Stromberg, Ed., "Surface and Colloid Science—Experimental Methods", Vol. II, (Plenum Press, 1979), pages 63-70. FIG. 2a provides a generalised figure demonstrating measurement of a contact angle.

The term "less hydrophobic" when comparing two surfaces means that the contact angle of a liquid droplet on a first surface is smaller or less than the contact angle of a similar liquid droplet on the second surface. Conversely the term may also refer to, for example, two hydrophilic surfaces which demonstrate a similar differential, i.e. one is more hydrophilic than the other. The term "hydrophobic" refers to surfaces having a contact angle of a liquid in air of at least 90 degrees. In contrast, the term "hydrophilic" refers to a material having a contact angle of a liquid in air of less than 90 degrees. FIG. 2b provides a generalised figure demonstrating the differences in contact angle between hydrophobic and hydrophilic surfaces.

Thus, because surface energies are most commonly quantified using contact angles the two at least partially opposing surfaces should exhibit a difference in fluid contact angle of at least 1 to 5°, about 10°, at least 20° or at and above 30°. Generally the surface having the lower surface energy should have a fluid contact angle of at least 90°, preferably at least 100°, more preferably at least 110°, most preferably at least 120°.

Generally liquid movement in micro or capillary channels by capillary flow is laminar, not turbulent, and as a result, not conducive for reagent/sample mixing. Surprisingly the inventors have discovered that, a difference in surface energies of two at least partially opposing surfaces encourages reagent mixing in a sample fluid without diminishing the fill velocity afforded by laminar flow as the fluid travels along a flow path. This, together with advantages of the size of the microchannels where diffusional mixing is of significant benefit overcomes a considerable problem with the reduction in size/scale of assay devices where turbulent mixing is hard or difficult to achieve.

Generally, "capillary flow" or "lateral flow" refers to passive flow of a liquid resulting from a capillary potential gradient or a surface potential gradient that can direct the flow of liquid via, for example surface tension. Capillary flow rate refers to the speed at which a sample front moves along a flow path, such as a membrane strip, when liquid is applied at one end. However, the rate decays exponentially as the liquid travels along the length. Therefore, the time required for a liquid to move along and fill a membrane strip or capillary tube of defined length is often measured and referred to as the capillary flow time, Capillary flow time is usually expressed in sec/cm and is inversely related to flow rate. The terms generally refer to the movement of a fluid on a surface wherein the fluid flows/travels in a particular direction or along a particular path. It should be noted that the term "lateral flow" is meant to be descriptive and not limiting, because devices could be configured in other ways with the same effect. For example, radial or vertical flow can easily be envisaged employing the same general principles. In particular embodiments the fluid coincidentally reacts with various reagents as it flows or travels.

The surfaces may comprise or consist of materials known in the art, such as, cardboard, glass, silicon, plastics and the like. Preferably the material comprises or consists of a hydrophobic material or has regions that are hydrophobic for example by being coated or laminated with suitable materials including, but not limited to, fluorinated materials such as fluoropolymers (e.g., polytetrafluoroethylene (PTFE)) and chlorofluoropolymers. Other materials which may prove suitable for altering surface energy include hydrocarbons such as petrolatum, latexes, paraffins, and the like.

The two at least partially opposing surfaces essentially function to support the steps of an assay procedure, such as a series of chemical reactions, which may take place on, in or between said surfaces. Thus, the assay device which comprises the surfaces may take a variety of forms, for example, a card, chip, cartridge or slide, and may be a single unitary element or form a part of a multi-component housing.

The two at least partially opposing surfaces may be substantially parallel surfaces. Thus, in one embodiment, one of the two at least partially opposing surfaces defines a channel, for so example in sunken or raised relief, the other of the two at least partially opposing surfaces forming a lid or seal closing the top of the channel. Alternatively the surfaces will be orientated with respect to each other at an angle of less than 180°. Thus in some embodiments the first and second surfaces may be angled adjacent to and with respect to one another forming angled channels in the form of a 'V'. In still yet other embodiments, one of the two at least partially opposing surfaces is generally planar and the other of the at least partially opposing surfaces may form columns or ridges on said surface, at an angle, for example of about 90° or less, forming an 'L' shape. It will be apparent to one skilled in the art that these variants are not mutually exclusive and may be combined.

The two at least partially opposing surfaces define at least one fluid flow pathway. A fluid flow pathway is for transfer of a fluid sample for example from a first region of the device to a second region of the device.

In one embodiment the two at least partially opposing surfaces define an open capillary channel: having a cross sectional geometry sufficient to create an open channel configured to form a closed capillary channel with the second of the two at least partially opposing surfaces.

Thus, the at least one fluid flow pathway may be a channel, groove, capillary, track or path and the like comprising physical side-walls, defined at least in part by the two partially opposing surfaces.

in another embodiment spacer elements are configured to hold the two at least partially opposing surfaces some distance apart to create a capillary channel between said surfaces.

The flow path will have a top and bottom surface spaced apart but without physical side-walls, and may be open (for example, to the atmosphere), relying on hydrophobic regions for liquid containment. Thus, in this embodiment, the surfaces are generally planar, substantially parallel surfaces separated by spacers and having a hydrophilic pathway defined there-between or thereon. In this case a sample fluid will travel by capillary forces between, and in contact with, the two surfaces, along the hydrophilic pathway but remaining confined by hydrophobic regions/areas. Thus, the two at least partially opposing surfaces and the fluid flow pathway may be configured in a number of ways.

Regardless of the configuration, when a sample fluid travels by capillary forces along, and in contact with, the two surfaces surprisingly the difference in surface energy between the two surfaces, and by extrapolation the difference in hydrophobicity/hydrophilicity, increases the tendency towards turbulence in a sample fluid as it travels with no apparent diminution in flow rate, in certain embodiments, and in relative terms, where one of the two at least partially opposing surfaces is an upper surface and the other of the two at least partially opposing surfaces is a lower surface, it can be envisaged that turbulence or 'circular' flow of the fluid may be further enhanced when the upper surface is a less hydrophobic or a hydrophilic surface whilst the lower surface is a less hydrophilic or hydrophobic surface.

In embodiments of the assay device, said device further comprises an application area in fluid communication with a first region of the device for introduction of a fluid sample.

An application area is a region on the apparatus at which an aqueous sample is introduced to—and is in fluid communication with—the fluid flow pathway. Generally there is a single application area from which at least one, two, three, four or more aliquots of an aqueous fluid sample may be taken for performing an assay or assays. Alternatively there may be a plurality of separate application areas for a number of different fluid samples or different aliquots of the same sample.

The term "aqueous sample" as used herein refers to any liquid sample, preferably one from which an analyte may be detected. Non-limiting examples of such samples include whole blood, serum or plasma samples, urine, cerebrospinal fluid (CSF), lymph, serous exudate or other biological fluids, animal tissue homogenates, deproteinised tissue homogenates, milk, raw egg, fermentation broths, animal feeds, and marine feeds. It should be appreciated that a sample need only be in liquid or aqueous form for at least an essential part of any assay. Thus, one skilled in the art could envisage that an assay may also be carried out at temperatures above the melting point of a sample, such as a wax for example, which is normally solid at room temperatures.

The assay device may comprise an aperture in one of the two at least partially opposing surfaces for introduction of a fluid sample to the application area.

One or other of the two at least partially opposing surfaces may comprise an aperture or apertures to facilitate or enable the application of a sample to the application area. The aperture is an opening in fluid communication with the application area and may be a moulded or drilled opening or simply an opening defined by the two at least partially opposing surfaces.

The assay device may further comprise at least one vent port, preferably located in the second region of the device.

A vent port is generally a small aperture preferably at the other end of a fluid flow pathway, i.e. remote from the first region, and connecting the capillary channel, to the atmosphere surrounding the device. A vent port allows for the movement of air or fluid from within to outside the device (or vice versa) equalising pressure between the device and the atmosphere which could otherwise inhibit capillary flow.

The assay device may comprise a flow stop junction between the first and second regions of the device configured to halt or pause capillary fluid flow of a fluid travelling between the two surfaces.

A flow stop junction is a region in the capillary channel into which the aqueous sample will not normally flow without the application of an outside external force. Such a junction has no moving parts generally relying on back pressure from surface tension of the liquid sample to stop fluid flow. It will be apparent that such back pressure can be created in a number of ways. For example, in certain embodiments, back pressure is created by increasing the cross-sectional area of the liquid flow pathway, i.e. capillary channel. The increase in cross-sectional area may be abrupt such as when a flow path of small cross-sectional area enters a larger, non-capillary chamber or gradual, for example, as the walls of a fluid flow pathway taper, diverge or widen over a distance. Alternatively, a junction may be created by using walls or barriers or modifying the surface properties of the interior of the device, such as by physical and/or chemical treatments, to decrease adhesion between the aqueous sample and the walls of the flow path, for example, forming regions substantially more hydrophobic than either of the two at least partially opposing surfaces. The flow stop junction may stop fluid flow completely for the remaining duration of the assay or it may simply bring about a temporary delay in liquid flow for a required time-period.

In certain embodiments, the assay device further comprises a filter membrane disposed between the application area and the at least one fluid flow pathway.

Cellular components of whole blood, such as red blood cells, may interfere with analyte assays such as cholesterol assays. Therefore, when the aqueous sample is blood, it is preferred that such cellular components are separated from the serum or plasma prior to analysis, ideally the separation is performed prior to the first step of the assay and is performed passively without the need for manual processing steps. Thus, the filter membrane or pad functions to remove particulates, such as blood cells, from the aqueous sample as the liquid travels by capillary action through the filter. Preferably the filter pad comprises or consists of at least one absorbent material.

The filter generally allows filtration of an aqueous sample before the sample is combined with reagents for performing an assay. The filter may be disposed within the aperture in one of the two surfaces in fluid communication/contact with the application area. Alternatively it may be situated between the application area and the fluid flow pathway.

The filter may be formed of a fibrous matrix to retard movement of, for example, red blood cells. Suitable materials include foams, glass fibres (such as borosilicate), sol-gel filters, chromatographic media such as filter papers or membranes such as nitrocellulose, polysulfone or polyester. In some embodiments, the filter may comprise reagents, for example, binding agents such as antibodies or beads which bind to and remove unwanted components from an aqueous sample. The filter may also comprise one or more pre-treatments, precipitating agents, surfactants/detergents, assay reagents, dyes, blocking agents or ligand binding inhibitors. Blocking agents and ligand binding inhibitors may limit the interference of particular components of the aqueous sample, for example Human Serum Albumin (HSA), with the assay. Thus, the filter may comprise an HSA extraction means such as anti-HSA antibodies for example, or any other means that uses for example precipitation, immobilisation and the like.

Generally the fluid flow pathway(s) of the assay device comprises at least one reagent selected from the group consisting of amphipathic polymers, dyes, probes, enzymes or ligand binding inhibitors.

The flow path may comprise reagents required for an assay or assays. For example, dyes, drugs, luminophores, antibodies, nucleotides, nucleic acid probes, primers, enzymes and the like. Different flow paths may comprise different reagents or combinations of reagents. A flow path may also comprise different reagents along its length, for example, allowing for sequential addition of reagents through capillary or lateral flow of the aqueous sample.

The fluid flow pathway or pathways may comprise one or more dyes or probes selected from the group consisting of Amplex Red, K37 and Nile Red.

Amplex Red (10-acetyl-3,7-dihydroxyphenoxazine), available from Invitrogen (catalogue numbers A12222 and A22177) amongst others, reacts with Hydrogen peroxide ($H_2O_2$) with a 1:1 stoichiometry to produce highly fluorescent resorufin. K37 (4-dimethylamino-4'-difluoromethyl-sulphonyl-benzylidene-acetophone) is disclosed by the inventors in their previous international patent application PCT/GB2005/004757. Nile Red, a lipophilic stain, also known as Nile blue oxazone, is available from Invitrogen (catalogue number N1142) or may be produced by boiling a solution of Nile blue with sulphuric acid. Nile Red stains intracellular lipid droplets red and is also intensely fluorescent, with a strong yellow-gold emission when in a lipid-rich environment.

The fluid flow pathway or pathways may comprise one or more enzymes selected from the group consisting of Cholesterol esterase, Cholesterol oxidase and Horseradish peroxidise.

Cholesterol esterase (Steryl-ester acylhydrolase, Registry number: EC 3.1.1.13) is an enzyme that catalyses the hydrolysis of cholesterol ester and some other sterol esters, to liberate cholesterol plus a fatty acid anion. Cholesterol oxidase (Cholesterol:oxygen oxido reductase, Registry number: EC 1.1.3.6) is an enzyme that catalyses the oxidation of cholesterol in the presence of molecular oxygen to 4-cholesten-3-one and hydrogen peroxide. Horseradish peroxidise (Sigma Aldrich, Registry number: EC 1.11.1.7) is a hydrogen peroxide oxidoreductase. Other equivalent hydrogen peroxide oxido reductases are known and may be derived from, for example, soy bean.

In other embodiments, the fluid flow pathway comprises one or more ligand binding inhibitors selected from the group consisting of alkali metal octanoate and octanoic acid. Suitable alkali metal octanoates include sodium octanoate and potassium octanoate The inventors have established that dyes/luminophores may bind to hydrophobic binding sites/domains of Human Serum Albumin (HSA) and may fluoresce when bound to HSA. HSA is a major component of blood serum having a concentration of approximately 30-50 mg/ml. The inventors believe that this additional fluorescence may cause a substantial background signal, potentially distorting measurements and leading to errors in the determination of concentration of lipoproteins.

HSA is known to have at least two types of binding site that are capable of binding various ligands. A first type is referred to herein as "a hydrophobic domain" which binds fatty acids whereas a second type of domain is referred to herein as a "drug binding domains" (which consists of two or more domains). These domains are known to one skilled in the art and are distinguished from each other in a paper in Nature Structural Biology (V5 p 827 (1998)). This paper identifies a hydrophobic domain as one to which fatty acids may bind whereas the drug binding domains are capable of binding a number of drugs that may be associated with HSA.

Thus, in preferred embodiments, the hydrophobic binding sites of HSA at which luminophores may bind, are blocked prior to analysis of a sample by addition of a ligand binding inhibitor.

The ligand binding inhibitor may be hydrophobic. The inhibitor may be amphipathic. The ligand binding inhibitor may comprise a fatty acid or a functional derivative thereof, as well as other hydrophobic molecules. Examples of suitable derivatives of fatty acid, which may block the hydrophobic binding sites of HSA may comprise a fatty acid, its esters, acyl halide, carboxylic anhydride, or amide etc. A preferred fatty acid derivative is a fatty acid ester.

The fatty acid or derivative thereof may comprise a C1-C20 fatty acid or derivative thereof. It is preferred that the fatty acid or derivative thereof may comprise a C3-C18 fatty acid or derivative thereof, more preferably, a C5-C14 fatty acid or derivative thereof, and even more preferably, a C7-C9 fatty acid or derivative thereof. It is especially preferred that the ligand binding inhibitor comprises octanoic acid (C8) or a derivative thereof, for example, octanoate: Preferably, the ligand binding inhibitor is added as an alkali metal octanoate, preferably a Group I alkali metal octanoate, for example, sodium or potassium octanoate.

Preferably, between about 10-400 mM of the ligand binding inhibitor is added to the sample prior to analysis, more preferably, between about 20-200 mM, and even more preferably, between about 30-80 mM is added. It is especially preferred that about 50 mM of the inhibitor is added as a final concentration. Hence, in a preferred embodiment of the method, about 50 mM of sodium octanoate may be added to the sample before analysis.

In particular embodiments a ligand or ligands may also be used to block the drug binding domain of HSA. Ligands for the drug binding domains of HSA include drug molecules such as: thyroxine, ibuprofen, diazepam, steroid hormones and their derivatives (drugs), haem, bilirubin, lipophilic prodrugs, warfarin, coumarin based drugs, anaesthetics, diazepam, ibuprofen and antidepressants (e.g. thioxanthine), benzoic acid or a derivative thereof (e.g. trichlorobenzoic acid or triiodobenzoic acid), fusidic acid or a derivative thereof. Alternatively the HSA binding domains may be blocked or removed by use of a HSA extraction means, for example, anti-HSA antibodies.

The assay device will generally comprise at least one detection zone configured for measurement of the result and/or progress of a reaction between at least a part of a fluid sample and the at least one reagent.

The detection zone may be a discrete region or area of the device or could simply be an area, point or region, for example, of the fluid flow pathway wherein the result and/or progress of a reaction between a part of the aqueous sample, such as an analyte, and at least one reagent is determined or measured. The at least one fluid flow pathway may transfer a sample fluid from the application area to the detection zone. The at least one fluid flow pathway is configured to be in fluid communication with at least one application area and a detection zone.

In certain embodiments, the apparatus comprises a plurality of fluid flow pathways and detection zones. Generally the at least one flow pathway connects, for example by fluid communication, the application area or areas with at least one detection zone. Usually the apparatus will comprises a single application area and one to eight, three to five or up to four flow paths leading to at least one to eight, three to five or at least four detection zones. It should be clear that the device may comprise varying numbers of flow pathways and detection zones and these may be of differing lengths and/or volumes. The application areas, flow pathways and/or detection zone are generally defined as being part or all of the capillary channel.

The result and/or progress of a reaction or assay which takes place on/in the assay device may be determined by means of optical measurement. Alternatively the result and/or progress of a reaction may be determined by visual inspection such as by colorimetry. In other embodiments the result and/or progress of a reaction is determined by means of fluorescence.

When the result and/or progress of a reaction is determined by fluorescence, the detection zone(s) may be arranged so that it may be brought into optical contact with excitation means of an assay reader. The detection zone should further be arranged such that the fluorescence produced from the assay may be detected by detection means of the assay reader. There may be separate detection zones for different aspects of the same assay or for different assays. Generally the detection zone(s) will be within or towards the second region of the device.

In one embodiment the assay device comprises at least three fluid flow pathways and at least three detection zones wherein, a first flow path is in fluid communication with the application area and a first detection zone, a second fluid flow pathway is in fluid communication with the application area and a second detection zone and a third fluid flow pathway is in fluid communication with the application area and a third detection zone.

When the assay device is for measurement of cholesterol and blood lipids, generally the first fluid flow pathway will comprise a first dye such as Amplex Red, the second fluid flow pathway will comprise a second dye such as K37 and the third fluid flow pathway will comprise a third dye, Nile Red. In this case the first fluid flow pathway may further comprise cholesterol esterase, cholesterol oxidase and horseradish peroxidise.

The use of enzymes in cholesterol and blood lipid assays is advantageous because cholesterol is often found in an esterified state, thus preferably cholesterol esterase is used to hydrolyse cholesterol ester to free cholesterol. Free cholesterol may then be converted to cholest-4-ene-3-one ketone by the action of cholesterol oxidase, generating hydrogen peroxide in the process. Advantageously, Amplex Red and hydrogen peroxide are converted to resorufin and water by horseradish peroxidase. Resorufin may then be detected as a fluorescent compound with an absorption maxima of about 563 nm and a peak emission wavelength of 587 nm. Total cholesterol content may be measured by exciting the sample at around 485 nm and measuring the resulting fluorescence at about 600 nm.

In some embodiments the fluid flow pathway may comprise an amphipathic polymer.

The inventors have found that amphipathic polymers may be used to coat surfaces, for example, plastics or glass or hydrophobic materials to further enhance fluid flow.

An amphipathic polymer is a polymer possessing both hydrophilic and hydrophobic properties. Such a compound may also be called an amphiphilic compound or a non-ionic hydrophilic polymer. In particular embodiments an amphipathic polymer is a substance which is soluble both in water and a wide range of organic solvents.

Amphipathic polymers may be used to promote fluid flow and/or mixing of aqueous solutions, for example with 'dry' components combined within or as layers above or below a coating of an amphipathic polymer. The use of amphipathic polymers also has the advantage that lateral flow of fluids is improved, for example, over the traditional 'wicking' with porous materials such as is disclosed in U.S. Pat. No. 6,485,982. Wicking methods of the prior art rely on the use of a support vehicle such as paper or a membrane through which liquid is drawn by capillary action. The use of amphipathic polymers removes the need for a support vehicle, such as a membrane, with the effect that liquids may travel greater distances or at greater speeds along, for example, microtubes, surfaces, hydrophobic surfaces and the like than by capillary action alone. Thus, through use of an amphipathic polymer the capillary flow rate is increased and/or the fluid flows/travels greater distances than would be expected by capillary action alone.

An amphipathic polymer may be used to coat a fluid flow pathway. Alternatively the amphipathic polymer may be in the form of a coating or film on the surface of the flow pathway or may be in the form of a powder, pellets, microparticles, nanoparticles, picoparticles or filling within a void or cavity of the flow path. Where the amphipathic polymer is a filling within a cavity it may fill the cavity entirely or may be a partial filling with, for example, gaps. The amphipathic polymer may form the flow pathway, for example, as a track or path on a hydrophobic surface along which fluid flow can occur. For example, the amphipathic polymer may be printed (such as by inkjet or bubble-jet printing), painted, sprayed or applied onto a surface, such as a flat surface, for example to form 'tracks' and/or layers. Reagents may be combined, such as by mixing, with the amphipathic polymer or may be arranged as layers above, below or beside the amphipathic polymer.

Polyethylene glycol (PEG) is an amphipathic polymer. Useful molecular weights of PEG include from about 600 to 10,000 Da, and between about 1000 to 3000 Da. Polyethylene glycol, also known as polyethylene oxide (PEO) or polyoxyethylene (POE)), is an oligomer or polymer of ethylene oxide. PEGs are available over a wide range of molecular weights from 300 g/mol to 10,000,000 g/mol. PEG has the following general structure:

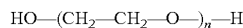

HO—(CH$_2$—CH$_2$—O—)$_n$—H

Numbers are frequently included in the names of PEGs to indicate their average molecular weights. For example, a PEG with n=80 would have an average molecular weight of approximately 3500 daltons and would be labelled PEG 3500.

Generally PEGs include molecules with a distribution of molecular weights. Whilst PEGs having different molecular weights find use in a variety of applications due to their differing physical properties, such as viscosity, their chemical properties are nearly identical. Different forms of PEG are also available dependent on the initiator used for the polymerization process, such as monofunctional methyl ether PEG (methoxypoly(ethylene glycol)), abbreviated mPEG. PEGs are also available with different geometries. Branched PEGs have 3 to 10 PEG chains emanating from a central core group. Star PEGs have 10-100 PEG chains emanating from a central core group. Comb PEGs have multiple PEG chains normally grafted to a polymer backbone. PEGs may also be covalently coupled to other molecules in a process known as PEGylation which may be advantageous when using the fluid flow properties of PEG for reagent mixing for example. Preferably when the amphipathic polymer is polyethylene glycol (PEG) it has a molecular weight of from about 1000 to 20,000 Da, more particularly between about 1000 to 6000 Da and yet more particularly from about 1000 to 3000 Da. Particularly useful PEGs include PEG2000, PEG6000, PEG12000 and PEG20000.

A further example of an amphipathic polymer is an amphipathic polypeptide, that is, a polypeptide which has a secondary structure such that the polypeptide has both a hydrophilic and a hydrophobic face. The design of amphipathic peptide structures (e.g., alpha-helical polypeptides) is known in the art. For example, in: Grell et al. (2001) J Pept Sci 7(3):146-51; Chen et al. (2002) J Pept Res 59(1):18-33; Iwata et al. (1994) J Biol Chem 269(7):4928-33; Cornut et al. (1994) FEBS Lett 349(1):29-33; Negrete et al. (1998) Protein Sci 7(6):1368-79. Other amphipathic or non-ionic polymers include polyvinyl alcohol (PVA) (Sigma Aldrich: 360627-25G), Carboxymethyl cellulose (Sigma: C-5678); O,O'-Bis(2-aminoethyl) PEG 2000 (polyoxyethylene bis (amine)) (Aldrich Chemistry: 14501) and PEG methyl ether 5000 (Aldrich Chemistry: 81323-250G) and other ionic polymers.

The use of an amphipathic polymer, particularly in combination with the embodiments described, may further assist in reducing the time an assay takes from several hours or even days to around as little as one minute.

In particular embodiments, the assay device is used for preparing lipid profiles and/or for conducting cholesterol and lipoprotein assays.

The assay device may be used to generate a patient's lipid profile by a taking a sample from a patient and then conducting the assay at the site where the sample is taken. Thus, the assay device should be adapted for a sample that may be any biological fluid, for example, blood, serum, lymph etc. The assay device may be adapted to determine the concentration of one or more of, for example, cholesterol, triglycerides, HDL, LDL, VLDL and IDL in a sample based on fluorescence analysis.

In another aspect of the invention there is provided a kit comprising a package of components for preparing a lipid profile or performing an assay, more preferably a cholesterol assay.

The kit may comprise one or more of a number of components such as (i) a means for sterilising a patient's skin prior to taking a blood sample, preferably by a finger prick sample. Conventional means is a piece of fabric or gauze which includes a sterilant such as an alcohol, or antibacterial agent such as bisbiguanides, for example chlorhexidine as a soluble salt in aqueous or alcoholic solution: (ii) skin penetrating means such as a conventional lancet device preferably comprising a safety sleeve. Alternatively the needle may be part of a conventional syringe assembly including barrel and plunger; (iii) an assay device according to the first aspect of the invention; (iv) gauze or adhesive plasters to cover the skin puncture wound; (v) instructional leaflets providing details on use of the device (vi) disposable gloves to avoid blood contact; (vii) an assay reader. The components of the kit may be supplied in a packaging means, such as a compartmentalised cardboard or plastic enclosure, preferably with a hermetically sealable cover.

DETAILED DESCRIPTION OF THE INVENTION

Figure 1A:
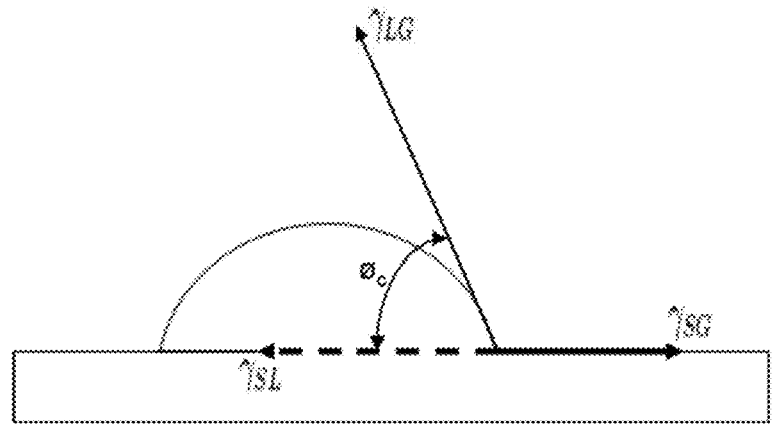
FIGS. 1A and 1B are generalised figures showing measurement of contact angle (ø).
Figure 1B:
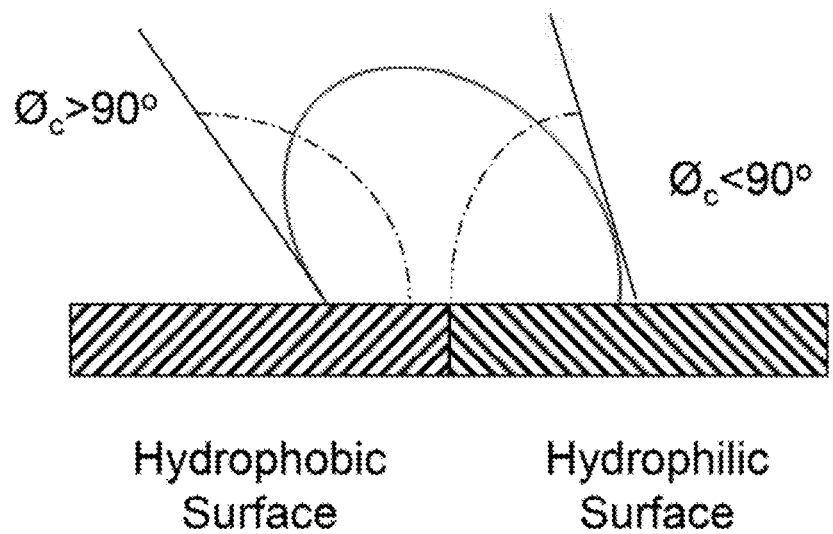
Figure 2:
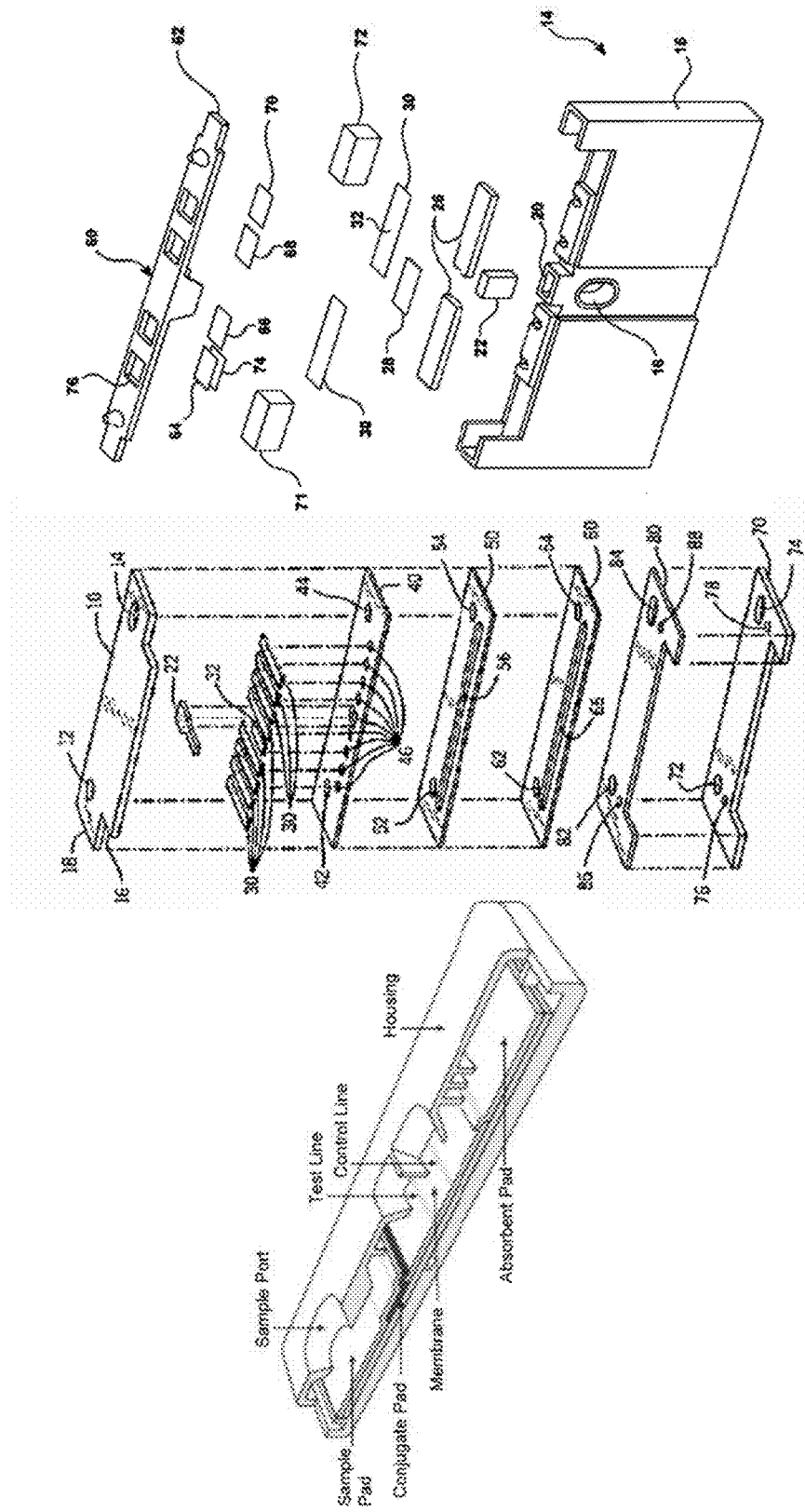
FIG. 2 provides examples of assay devices of the prior art.
Figure 3A:
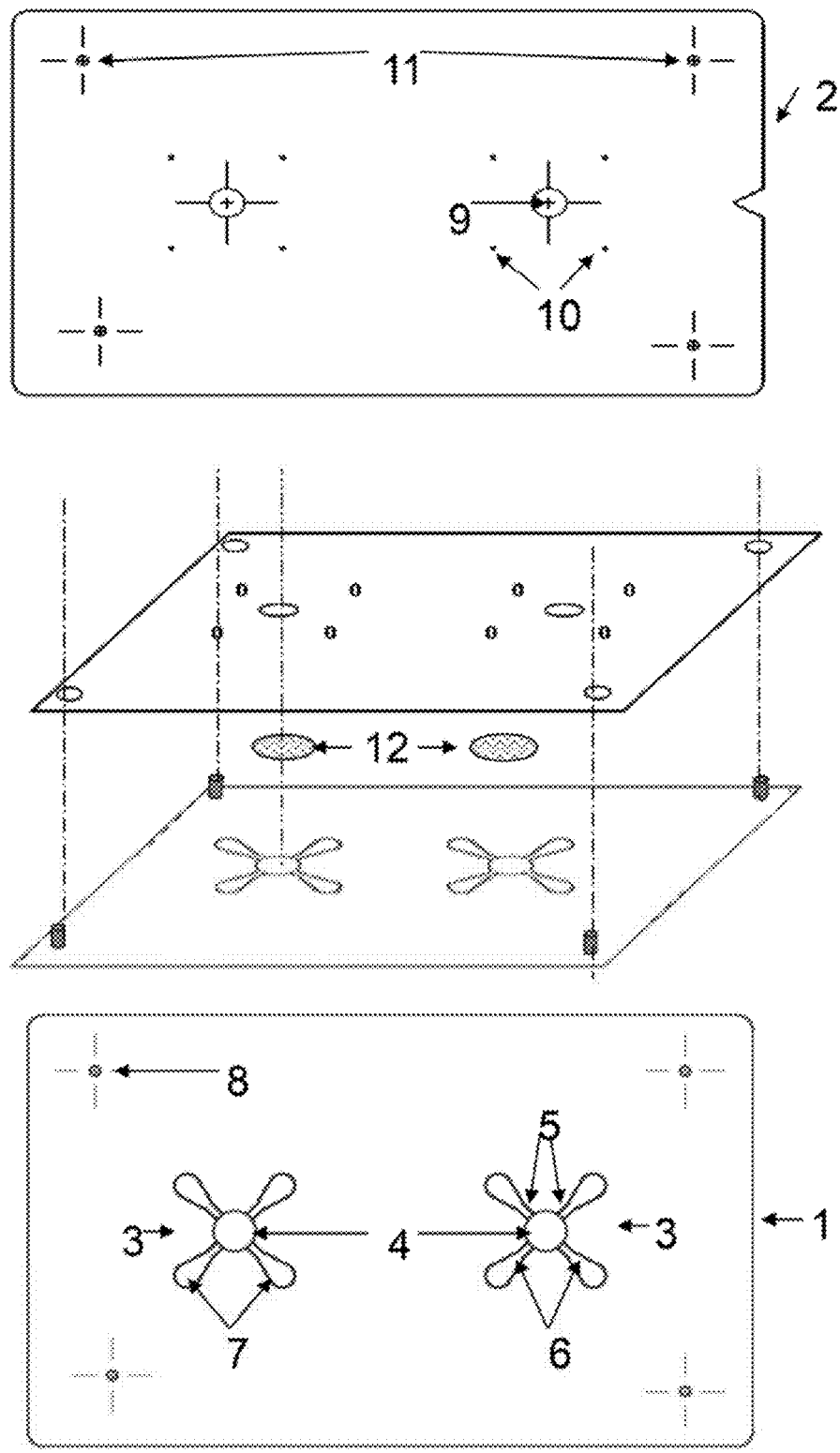
FIGS. 3A and 3B illustrates one embodiment of the assay device which uses a 'tear drop' shaped stop flow junction.

FIG. 3a illustrates one embodiment of an assay device according to the invention which may be used, for example, in the determination of lipoprotein levels in blood.

In this embodiment, the assay device comprises a first, support surface (1). The support surface generally comprises or consists of an opaque material, for example a plastics material incorporating an amount of a pigment such as carbon black. In this case, a support surface is formed from a medical grade polymer compatible with fluorescent, luminescent or photometric measurement. Cyclic olefin polymers generally have excellent mechanical properties, low autofluorescence and high UV transmission. Suitable polymers include cyclic olefin copolymers such as Topas® COC (CAS number 26007-43-2), Zeonor® COP, Zeonex® COP or Udel® polysulfone (CAS Number 25135-51-7). In this example the support is formed of TOPAS COC comprising 1% Carbon black. The use of carbon black has the added advantage that, during laser welding for example, the power requirement is reduced increasing ease of manufacture of the device and protecting heat labile components in the reaction chambers. The use of Carbon black may also have benefits relating to heat dissipation/insulation.

The incorporation of pigments, such as carbon black, into plastics alters the surface energy of such plastics and by extension, their hydrophobicity/hydrophilicity. This has the advantage that surface modification, for example chemical modification, is not required to create a difference in surface energy between the first, support, surface (1) and the second surface—in this instance a cover member (2).

The support surface of this embodiment is moulded but may be formed by any standard moulding or machining techniques known in the art, Whilst it is generally flat, it comprises profiled areas, in this example of sunken-relief which form, in this case four, capillary channels (3) arranged circumferentially around an application area (4). In this case each of the four channels are equidistantly spaced from one another at an angle of around 90°.

The moulded support surface forms an application area (4), fluid flow paths (5) and detection zones (6).

Figure 3B:
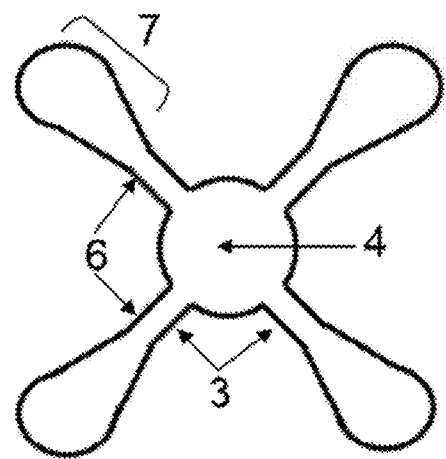
Figure 4:
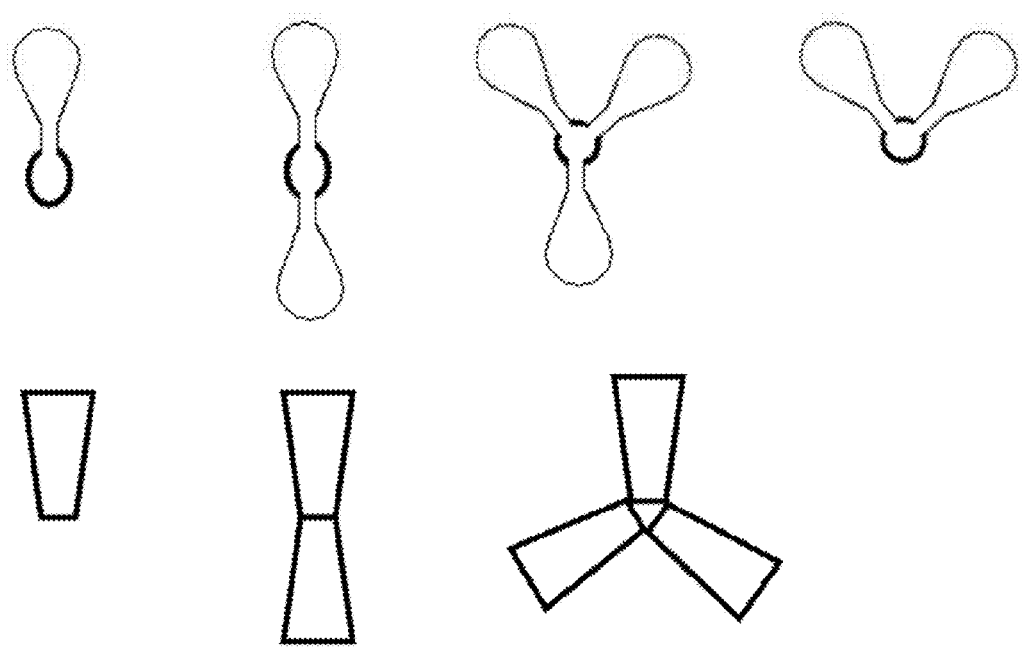
FIG. 4 illustrates alternative assay layouts/formats.

Each end of the fluid flow pathways (5) farthest from the application area (4) is characterised by a gradual taper of one or more of the capillary channel walls. This taper increases the width and/or depth and by extension the cross-sectional area of the capillary flow channel forming a stop flow junction (7) preventing further capillary fluid flow. Here, the channel forms a bulbous end but may take a variety of other forms. The structure of the capillary channel which defines the application area, fluid flow pathway, detection zone and stop-flow junction is shown more closely in FIG. 3b. It will be apparent to one skilled in the art that the channels may be arranged in any number of formats or be of differing shapes to suit a particular assay. For example, and by way of non-limiting example, the channels may be ovoid or 'teardrop' shaped, trapezoidal, triangular, columnar or tubular. Further examples, are shown in FIG. 4. For hospital, laboratory or large volume use, it is conceivable that 10-20, 20-40, 40-60 or 50-100 capillary channels could be arranged on an assay device the size and shape of a compact disc.

Figure 5:
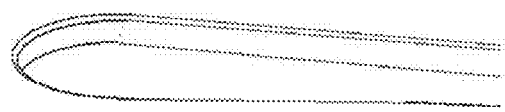
FIGS. 5, 5A, 5B and 6 illustrate alternative configurations of the fluid flow pathways, stop flow junctions and a further embodiment of the device.
Figure 5A:
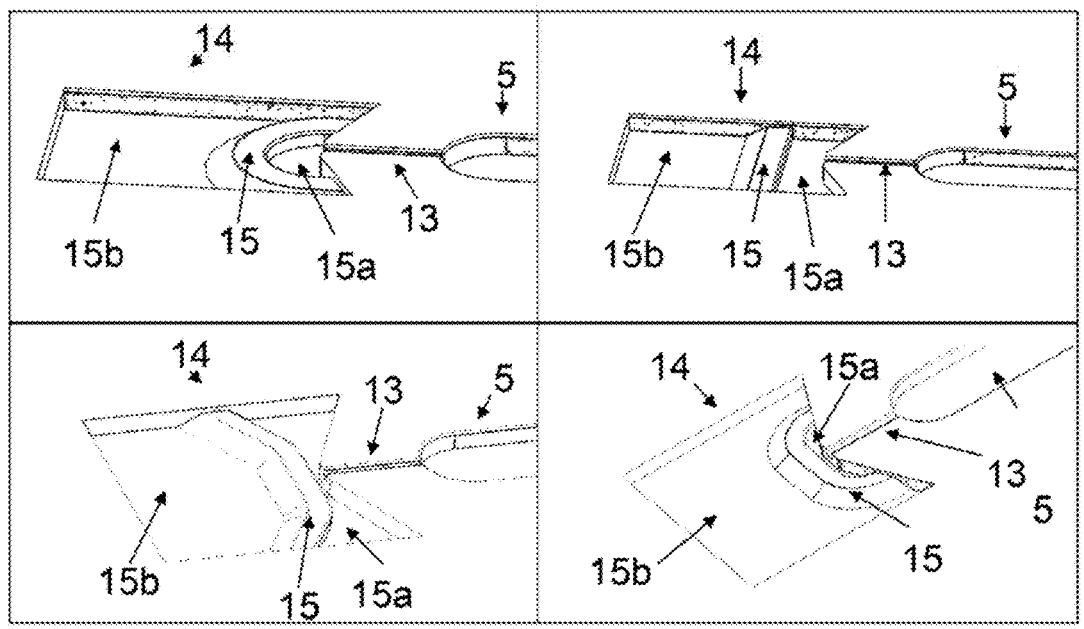
Figure 5B:
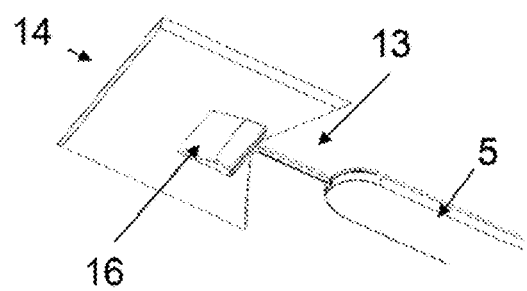
Figure 6:
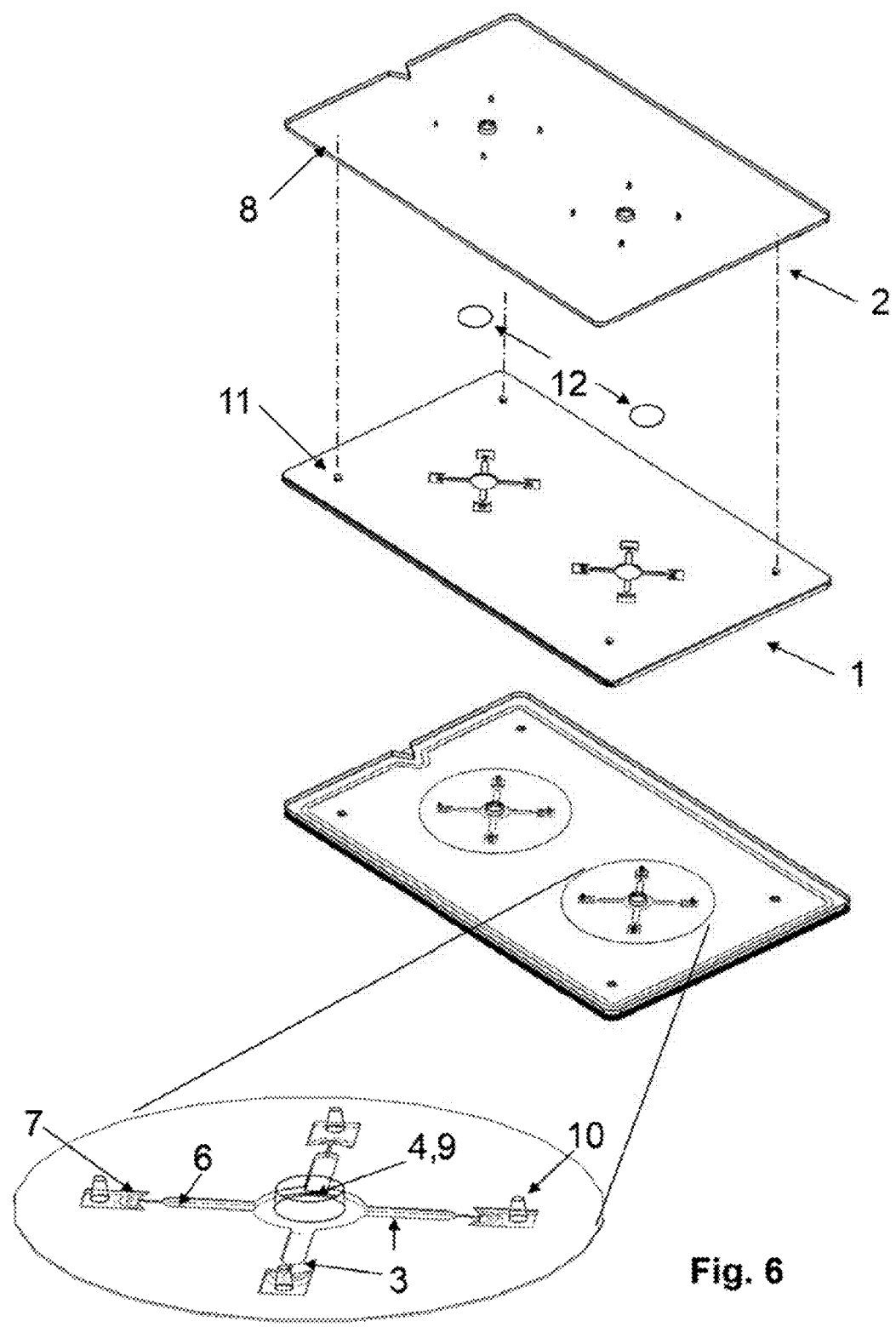

FIG. 5 illustrates further embodiments of stop flow junctions. In FIG. 5a the fluid flow pathway (5) maintains an even cross-sectional area along substantially its entire length before narrowing or constricting to form a section of fluid flow pathway of reduced cross-sectional area (13) towards the distal end. This section of fluid flow pathway is in turn adjacent to, and in fluid communication with a chamber (14). The chamber is divided into regions by a low wall or barrier (15)—in this case into two parts (15a) and (15b). In use, a fluid enters the chamber (14) filling part (15a). The wall (15), or more accurately the capillary forces acting on the sample fluid in the region of the wall, stops flow of fluid into the second part of the chamber (15b). In FIG. 5b the wall is replaced by a raised portion (16). Again, capillary forces acting so on the sample fluid in the region of the raised portion (16), prevents fluid from filling the whole of the chamber. One skilled in the art will realise that the configuration (for example size, shape, height) of the chamber (14) and wall (15) or raised portion (16) may take a number of forms including different geometric shapes such as circles, trapezoids and the like. A vent port located adjacent to the second part or distal region of the chamber (15b) allows for movement of air from within the chamber to the atmosphere equalising pressures within the fluid flow pathways of the device.

The support surface also comprises a number of alignment posts (8) to align the support surface with the second surface—the cover member (2).

The cover member (2) is also formed from a suitable medical grade polymer such as those described above. In this example the cyclic olefin copolymer (Topas COG), CAS number 26007-43-2 was used again but in this case without carbon black. As a result the cover member is optically clear/transparent—at least to the excitation/emission wavelengths of the assay reader.

The cover member (2) is also moulded and generally flat comprising a number of apertures. The cover member is mountable with the support member, optionally comprising a gasket or spacer element positioned there between. Aperture (9) is aligned with the application area and allows a user to apply a fluid sample to the application area. A further series of smaller apertures function as vent openings (10).

In the embodiments shown, alignment holes (11) orientate the cover member with respect to the support member by accommodating the alignment posts (8). In alternative embodiments the apertures and alignment holes are provided in the support member, the cover member simply fulfilling the role of a cover.

The Alignment elements may simply be raised members with corresponding alignment holes or grooves. The support and cover members may be fixed or bonded together for example by mechanical means such as by use of screws, rivets, bolts or tabs. Alternatively the support and cover members may be held together by friction fit. In other embodiments the cover and support members are bonded together, for example by use of glues, solvents, adhesive tape and the like, in this case the cover and support members are bonded together by use of heat and laser welding.

One or both of the support and cover members may comprise identification means, to provide a unique identifier and/or to provide a means for an assay reader, for example, to monitor the number of times an assay device has been used or when sample was applied so that an appropriate assay time passes. Such identification means may also contain instructions or data such as calibration or quality control data. Identification means may take a variety of forms including, but not limited to, text, Braille, numerical data, linear bar code(s), 2D bar code(s), RFID tag(s) and the like.

A filter (12) is held firmly between the support and cover members adjacent to and in fluid communication with the application area (4) and aperture (9) and the fluid flow pathways.

In use, either an undiluted or diluted sample is applied directly to the filter via aperture (9).

The assay device may be utilised to test whole, venous, blood, for example, obtained by finger prick or in the case of neonates, a heel prick. This is a way of opening a small wound, for example in the finger tip, which produces no more than a few drops of blood (~less than 50 µl such as from about 10 µl to 20 µl). After a blood droplet has formed it can be applied directly to the application area of the assay device or sucked up by a pipette and then applied accordingly. The ability to utilise blood obtained by, for example a finger prick, directly represents a significant advantage over assays known in the art.

Alternatively the assay device may be utilised to test a sample that is derived from plasma, in which case a 1 in 80 dilution of the sample may be performed. Generally the diluent that is used is phosphate buffered saline (PBS) and it may comprise at least one ligand binding inhibitor. The diluent may also comprise two ligand binding inhibitors, one for the hydrophobic binding site(s) and one for the drug binding site(s).

Fluid in the sample migrates through the filter and as it does so red blood cells, in the case of whole blood, and large particulates are removed by passive filtration. As a result background interference from such cells or large particulates is reduced. In this example, the filter further an HSA extraction means comprising anti-HSA antibodies which remove HSA from the sample as previously discussed, again reducing background.

The fluid travels by means of capillary flow from the application area (4) into the fluid flow pathways (5) with which the application area is in fluid communication. As it travels the liquid hydrates reagents in dry form, such as fluorescent dyes and enzymes, and mixes with them. Thus, the sample moves by capillary or lateral flow not requiring the application of external forces, such as pumps, to move the aqueous sample.

Use of the term 'dry form' refers to components that are maintained in a form in which they are generally substantially free from, or depleted of, liquid or moisture; that is they are not in solution until reconstituted by the performance of the assay itself, rather than being reconstituted prior to and separate from the assay procedures. Thus, the aqueous sample itself reconstitutes the dry reagent or reagents, thereby eliminating the need for separate reconstitution buffers and steps.

Where enzymes or other reagents are used, particularly where they are used in dry form, it is preferred that such enzymes or other reagents are stabilised. In the context of this invention, a 'stabilised reagent' is a reagent that has improved stability with respect to, for example, storage stability, thermal stability etc. Thus, in particular embodiments the reagents that are used comprise a stabilising agent. Particular stabilising methods are disclosed in International Patent Application numbers WO90/005182 and WO91/014773 the contents of which are hereby incorporated by reference. Other suitable stabilising reagents include copolymers of vinylpyrrolidone and dimethylaminoethyl methacrylate, for example, sold by international Speciality Products under the trade name Gafquat®. Gafquat (CAS Registry Number: 53633-54-8; 7732-18-5) is the name for a range of water-soluble copolymers such as Polyquaternium-11.

The difference in surface energies between the support and cover members with which the fluid sample is in contact increases mixing of the fluid with the dry reagents.

As the fluid front moves forward, an equivalent volume of air is displaced through the vent openings equalising pressure within the device. Once the fluid reaches the stop-flow junction, surface tension prevents further capillary flow.

At this stage the device can be placed within a suitable assay reader and the levels of analytes, in this case cholesterol and blood lipids, are measured.

The housing of the assay device is usually adapted to enable it to be placed in functional communication with an assay reader. For example, the assay device may be inserted into, placed on or attached to the reader and the reader may comprise docking means, such as a slot, or alignment means to enable the assay device to be inserted, placed or attached appropriately. In this embodiment, the assay device has a 'V'-shaped cut out in the cover member which facilitates alignment of the assay device with a reader. Generally the assay device of the present invention is a disposable whilst the reader will usually be reusable.

The assay device may be used for a variety of assay processes or reactions such as immunoassays and fluorometric assays including cholesterol, lipoprotein or triglyceride assays.

An immunoassay is a biochemical test that measures the concentration of a substance in an aqueous sample, for example serum or urine. The assay utilises the reaction of an antibody or antibodies to its antigen taking advantage of the specific binding of an antibody to its antigen. Preferably monoclonal antibodies are used since they bind to one site of a particular molecule providing specific and accurate tests. Both the presence of antigen or antibodies may be measured, for example, when detecting infection the presence of antibody against the pathogen may be measured. Alternatively when measuring biological molecules such as hormones, and the like, the hormone biological molecule may acts as the antigen. The response of the aqueous fluid being measured may be compared to standards of a known concentration, for example, plotting of a standard curve on a graph. Detecting the quantity of antibody or antigen may be achieved by a variety of methods such as labelling either the antigen or antibody. By way of non-limiting example, the label may consist of an enzyme (EIA or ELISA), a radioisotope such as I-125, a magnetic label or a luminescent or fluorescent label.

Advantageously, the device of the present invention relies on capillary flow for fluid transport of low volume samples and there is therefore no need to use moving parts. Thus, the device overcomes problems of scale, economy, manufacture and mechanical failure encountered in the prior art.

An assay reader for use with the assay device of the present invention may be adapted to receive two or three assay devices, for example, from multiple patients or for multiple tests of an aqueous sample from an individual patient. Such a reader may comprise two (or more) excitation means that can be aligned with the detection zones of the assay device. 'Excitation means' are operable to excite the sample in the detection, for example, so that it fluoresces. The apparatus will also comprise at least one detection means which are operable to detect, for example, the fluorescence emitted by the sample at the detection zone(s).

Generally the excitation means comprises an illumination source operable to illuminate the sample at about 400 nm-600 nm. Accordingly the light source is preferably capable of illuminating the sample at between about 400 nm-600 nm. The illumination source may comprise one or more a bulbs, or one or more LEDs, or other sources such as a one or more lasers. Excitation wavelengths may be varied utilising at least one interference filter. The excitation means may also comprise polarising means operable to polarise light produced by the illumination source. The excitation means may also further comprise focussing means adapted to focus the light on to the sample. The focussing means may comprise a lens, or light guide such as a fibre-optic filament or optical light film (3M).

The detection means may comprise a photodiode, CCD, or photomultiplier or optical sensor, which is preferably yellow-red sensitive. Fluorescence emitted by the sample may be detected within a range including about 440 nm-650 nm depending on the dye or dyes used. The detection means should be able to detect fluorescence emitted at about 490 nm, about 495 nm, about 570 nm, about 600 nm and about 610 nm. The fluorescence may be collected by a second lens, and may pass through a polariser. Scattered excitation light may be removed by a cut-off filter(s) or band pass filter(s). For measurement of the fluorescence intensity, the current from the photodiode or the count rate from the photomultiplier may be read from an ammeter, voltmeter, or ratemeter module. Other means will be apparent to one skilled in the art.

The reader may also comprise an excitation correction system so that fluctuations of in the light source may be accounted for. The apparatus may comprise at least one fluorescence standard for use in calibrating prior to determining the concentration of an analyte or analytes. The standard may be an internal standard.

In particular embodiments the assay reader is configured to detect and measure the fluorescence intensities of a single or a plurality of assays simultaneously or in turn as the assay device enters the reader or at some time thereafter.

The reader may also comprise processing means adapted to determine the concentration of an analyte or analytes in the sample based on the fluorescence detected.

The reader may further comprise display means for displaying measurements determined from the sample, preferably as a read-out. For example, the display means may comprise an LCD screen, or may rely on a computer for powering and/or computing and/or display. In its most basic form, the display means may simply be a window in which an indication or measurement is displayed.

Usually, the assay reader is portable and advantageously, the assay device and reader may be used to carry out assays simply, rapidly and simultaneously to determine the presence/absence or concentration of an analyte from an aqueous sample such as a biological fluid. For example, a clinician with knowledge of cholesterol, lipoprotein and HDL concentrations can use the device to decide on an effective course of treatment. In addition, the assay device and reader is portable and may be used by GPs, or nurses who carry out home visits, or even as test kits for home use.

In this case, the processing means are adapted to directly determine the concentration of one or more of, for example, cholesterol, triglycerides, HDL, LDL, VLDL and IDL in the sample based on fluorescence analysis. Alternatively, the processing means may be adapted to calculate the concentration of LDL, VLDL and IDL, in the sample based on the concentrations of total lipoprotein, cholesterol and HDL.

Use of the Device in Analysis of Cholesterol and Lipids

The following example describes a method of measuring lipoproteins in an aqueous biological sample using an assay device of the present invention.

In this example, the fluid flow pathways are coated with an amphipathic polymer, PEG, to speed up fluid transport. For lipid profiling the amphipathic polymer is also combined with a fluorescent dye such as Amplex Red, K37 or Nile Red and/or other reagents such as enzymes, laid down or printed within the fluid flow pathway(s) or within the detection zone.

The fluorescent dye(s) and/or other reagents may be printed as one or more arrays of pico-litre droplets. Suitably such an array may comprise between about 150 to 4500 droplets along a first axis by 25 to 100 droplets along a second axis, Particular sizes of array include about 3400×65 droplets, about 3000×65 droplets, about 1500×65 droplets, about 1900×65 droplets, 600×65 droplets, 450×65 droplets or about 400×65 droplets per $mm^2$. It will be apparent to one skilled in the art that, whilst these droplet densities may be varied with little effect on assay performance, it will also be apparent that conversely such densities can also be optimised to improve assay performance. For example, the droplets could also be applied as nano- or femto-litre droplets, applied as overlapping arrays, applied one (or more) on top of another, applied as discrete individual arrays, spaced apart or applied as blocks of several arrays forming an array of a larger size (i.e. additive). The array size may also be optimised with respect to a particular reagent or dye concentration for example.

When 'printing', droplets of fluorescent dye may be applied to the device at concentrations of between about 0.1 mM to 3.0 mM, more suitably, between about 0.3 to 2.5 mM, and even more suitably, between about 0.5 to 2.0 mM. Alternatively, when the device is for use with diluted blood samples, the concentration of fluorescent dye may be between about 0.8 to 1.2 mM. A useful concentration of fluorescent dye is 1.0 mM and for undiluted blood samples a useful concentration is about 2.0 mM. The dye is subsequently dried before use.

In use the sample fluid hydrates the amphipathic polymer and dilutes the fluorescent dye which can then bind to lipoproteins in the sample. When so bound the dye fluoresces under appropriate excitation. The total lipoprotein concentration in the sample may be determined using fluorescence analysis.

The method generally comprises:
(i) contacting an aqueous biological sample with at least one dye or luminophore and optionally at least one amphipathic polymer wherein, the at least one dye or luminophore binds to at least one lipoprotein in the aqueous biological sample and when bound thereto fluoresces under appropriate excitation:
(ii) exciting the product(s) from step (i) at an excitation wavelength of between about 400 nm-620 nm;
(iii) measuring the fluorescence emission following step (ii) at a wavelength of between about 440-650 nm.

The method may be used to prepare a lipid profile from an aqueous biological sample.

By use of the term "total lipoprotein", is meant the collective concentration of at least VLDL, HDL, LDL, IDL and chylomicrons in other words, the sum of the concentrations of triglyceride and total cholesterol in a sample. By use of the term "total cholesterol", is meant the total concentration of cholesterol in a sample. By use of the term "lipid profile", is meant the concentration(s) or relative concentration(s) of lipid components (i.e. total lipoproteins and total cholesterol and triglyceride) in a sample.

Most lipids present in a blood or serum sample are bound to lipoproteins. Conventional tests conducted in clinical labs do not measure total lipoprotein. Hence, conventionally, it is required to first determine, and then add the concentration of cholesterol and cholesterol esters, to that of triglyceride to determine the total lipoprotein concentration. Conventional measurement of triglyceride in a clinical lab is subject to substantial errors because it relies on the measurement of glycerol, which circulates naturally in the blood. Advantageously, because the number (volume) of lipoprotein particles is measured directly to determine the concentration of total lipoprotein (which equates to the total lipid concentration) the cholesterol assay according to the present invention is not subject to this error. Thus, errors such as in the triglyceride concentration caused by circulating glycerol in the sample are obviated.

In their previous International patent application PCT/GB2005/004757, published as WO2006/061646, the inventors developed a simplified assay based on the use of, for example, K37 for measuring lipoproteins in a biological macromolecule that is particularly useful when a clinician wishes to quickly and efficiently obtain a lipid profile. For determining the concentration of total lipoprotein (i.e. HDL, LDL, IDL and VLDL) in a blood sample using K37 fluorescence measurements, the inventors realised that the fluorescence response from K37 bound to the various lipoprotein classes can be made substantially the same for a given total lipoprotein concentration, i.e. total lipoprotein concentration, irrespective of its composition (i.e. the ratio of HDL:LDL:IDL:VLDL in the sample). Accordingly, it is preferred that K37 is used in such a manner that the response of fluorescence intensity is substantially linear across the range of concentrations of lipoprotein molecules that would be expected from samples that would be encountered in clinical tests.

Not wishing to be bound by any hypothesis, it is believed that the intensity of fluorescence from the fluorescent dye depends on its affinity for a particular lipoprotein molecule (HDL, LDL, IDL or VLDL) in the sample. The quantum yield of fluorescence depending on the environment within that lipoprotein molecular complex, and also the degree of fluorescence quenching caused by energy transfer between probe molecules packed closely together. Hence, in their previous application, the inventors reasoned that it would be possible to select a suitable concentration of the probe substance and excitation and emission wavelengths that may be used to make an accurate measurement of total lipoprotein by simple fluorescent measurement. The inventors further realised that such a concentration of probe would preferably balance K37's higher quantum yield in HDL compared to VLDL and LDL with its higher affinity for HDL, and therefore a higher degree of quenching within HDL to produce a constant fluorescence signal response over all lipoprotein particles.

The inventors have conducted a series of experiments to investigate whether it was possible to obtain a linear and equal relationship between the fluorescence of the probe substance, K37, and the lipoprotein concentration for each lipoprotein particle type (HDL, LDL, and VLDL), across the range of lipoprotein concentrations that would be encountered in real serum clinical samples. To their surprise, they found that there was a defined concentration of K37 and particular excitation and emission wavelengths at which there was a linear relationship between the fluorescence of K37 and lipoprotein concentration. Thus, using the methodology of their previous patent application (PCT/GB2005/004757) the skilled person may identify other suitable dyes that also demonstrate such a relationship with lipoprotein concentration.

The use of enzymes in a cholesterol assay is advantageous because cholesterol is often found in an esterified state, thus preferably cholesterol esterase is used to hydrolyse cholesterol ester to free cholesterol. Free cholesterol may then be converted to cholest-4-ene-3-one ketone by the action of cholesterol oxidase, generating hydrogen peroxide in the process. Advantageously, Amplex Red and hydrogen peroxide are converted to resorufin and water by horseradish peroxidase. Resorufin may then be detected as a fluorescent compound with an absorption maxima of about 563 nm and a peak emission wavelength of 587 nm. The total cholesterol content can be measured by exciting the sample at around 485 nm and measuring the resulting fluorescence at about 600 nm.

When an enzyme is utilised it may be provided at a level many times in excess of the ratio that would be used for measuring, for example, the enzymes Km, for example. Such a ratio may be extremely high when compared to those used in the art which are around 1:1000. Surprisingly, the combination of a difference in surface energies of the device coupled with the use of dry stabilised enzymes and optionally an amphipathic polymer enables far smaller quantities of both sample and reagent to be used. Not wishing to be bound by theory, it is believed that the difference in surface energies of the two at least partially opposing surfaces creates a circular motion within the laminar flow of the aqueous sample leading to more efficient mixing. As a result of this increase in efficiency, larger levels of enzyme may be used in smaller reaction volumes leading to yet more efficient and faster reactions than those previously possible in the methods of the prior art.

The second step for the method may comprise:

(ii) exciting the product(s) from step (i) at an excitation wavelength of between about 400 nm-520 nm.

The excitation wavelength may be between about 420 nm-480 nm or between about 440 nm-470 nm. The excitation wavelength or wavelengths used will depend on the specific fluorescent dyes being used in the assay. For Amplex red the excitation wavelength is about 480 nm, for K37 the excitation wavelength is about 440 nm and for Nile Red the excitation wavelength is about 580 nm.

A third step of the method comprises:

(iii) measuring the fluorescence emission at a wavelength of between about 490-650 nm.

Alternatively the fluorescence emission can be measured at a wavelength of between about 520 nm-620 nm. At emission wavelengths of about 540 nm, or higher, more accurate readings for determining the total lipoprotein concentration (i.e. the concentration of HDL, IDL, LDL and VLDL, but also chylomicrons if present) may be observed. However, the preferred fluorescence emission wavelength(s) that is/are measured will depend on the specific fluorescent dyes being used in an assay. For Amplex Red the fluorescence is measured at so about 600 nm, for K37 fluorescence is measured at about 495 nm and for Nile Red fluorescence is measured at about 610 nm.

It should be appreciated that the excitation and emission wavelengths need not be measured at the optimal wavelengths for each specific dye. Wavelengths may be selected that give the best separation or performance when the dyes are used either in combination or in parallel, for example when the assays are performed at the same time in a single assay device. It will be apparent that steps (ii) and (iii), excitation and detection, may also be carried out substantially simultaneously.

In addition, the concentration of triglyceride may be calculated by subtracting total cholesterol concentration from the total lipoprotein concentration. Hence, a more detailed lipid profile of the sample is thereby generated consisting of total lipoprotein concentration, total cholesterol concentration, and also triglyceride concentration, which would be useful to the clinician.

The inventors have previously discovered that a number of dyes will bind to lipoproteins and exhibit different fluorescent responses that are dependant on the particular lipoprotein bound. Fluorescent measurement of these dyes makes it possible to distinguish between the types of lipoprotein present in a sample. This is done by comparing the enhanced or reduced fluorescence caused by one type of lipoprotein in a lipoprotein mixture with the fluorescence expected from the other lipoproteins (in the absence of the specific propertied lipoprotein) as determined from a calibration curve and a known value of the total lipoprotein content. For example the fluorescent dye, Nile Red, exhibits a significantly higher fluorescence in HDL than in other lipoproteins, such as LDL and VLDL. Therefore, other fluorescent dyes (e.g. Nile Red, K37 or any other lipophilic probe that shows specificity, or fluorescence enhancement or reduction towards a particular lipoprotein), may be used to discriminate between classes or subclasses of lipoproteins in the sample.

Accordingly the method of the invention enables the determination of the concentration of a particular class, or sub-class of lipoprotein in a sample using fluorescence analysis. Generally this involves determining the concentration of a particular class or sub-class of lipoprotein by the shift in fluorescence response of a dye specific to that lipoprotein using a second and/or third fluorescent dye.

By way of example, in order to determine the HDL concentration in a sample using Nile Red, a calculation is made of the excess fluorescence from Nile Red due to the presence of HDL. Firstly, the total lipoprotein concentration (measurement "A") is measured by the linear correlation of K37 fluorescence with lipoprotein concentration (as determined by step (i)). Secondly, Nile Red fluorescence is then calibrated with LDL (and/or VLDL as the fluorescence to concentration response must be essentially the same) at various concentrations to obtain a calibration curve with slope "X" and intercept "Y". A skilled technician would know how to prepare a range of concentrations of LDL (and/or VLDL), and determine the respective fluorescence for each concentration.

Calibration curves may be constructed for a series of concentrations of HDL and a constant concentration of LDL to give slope "Z". Knowing the total lipoprotein concentration from the K37 measurement "A" and the excess Nile Red fluorescence of the unknown sample "B", the concentration of HDL "C" in the unknown sample can be determined by the following equation:

$$C=(B-(AX-Y))/Z$$

It will be appreciated that, in practice, pre-prepared or standard calibration curves may be used. Furthermore assay devices of the present invention or assay readers for use with such devices developed to generate lipid profiles may comprise internal standards and/or have processing means that will allow for automatic calculation of lipoprotein concentrations without user intervention.

Therefore, it will be appreciated that fluorescent measurements may be used for determining the concentration of HDL, VLDL (by calculation), LDL (by calculation), total lipoprotein, triglycerides (by calculation) and also total cholesterol. All these parameters may be determined simultaneously, in parallel, by exciting and measuring fluorescence over a similar range of wavelengths. As discussed above, this is a considerable improvement over conventional assays, which have to be carried out separately, and often in dedicated laboratories, causing a delay in the generation of results. In addition, the fact that multiple lipid parameters can be measured at the same time considerably simplifies the instrumentation required to carry out the measurements.

The lipid profile generated includes the determination of the concentration of cholesterol bound to LDL in the sample. It is especially advantageous to know the LDL cholesterol concentration as it is highly atherogenic. Hence, the method provides a multi-readout of at least three, preferably four or five, or more parameters of the lipid composition in the sample. Furthermore, it is possible to calculate/estimate the concentration of Cholesterol-VLDL-Cholesterol from the triglyceride concentrations, as it is generally assumed that most of the triglycerides are carried in VLDL and the cholesterol component of VLDL is 20%. This is particularly advantageous for helping the clinician to decide on a suitable course of treatment.

Experimental Overview

The following experimental details describe the complete exposition of one embodiment of the invention as described above.

EXAMPLE 1

Total Cholesterol Assay

The assay utilizes a triple enzyme system capable of converting one molecule of cholesterol or cholesterol ester into a molecule of hydrogen peroxide ($H_2O_2$). The hydrogen peroxide generated is then used to oxidize the dye Amplex Red (non-fluorescent) to generate the highly fluorescent product Resorufin.

Stabilization of Enzymes onto Plastic

The total cholesterol assay uses the following enzymes and dye:
 Cholesterol Esterase (3.1.1.13)
 Cholesterol Oxidase (1.1.3.6)
 Horseradish Peroxidase (1.11.1.7)
 Amplex Red: 10-acetyl-3,7-dihydroxyphenoxazine Enzymes were stabilized onto plastic using Gafquat as a stabilizing agent. The three enzymes were added to a solution of 0.01M potassium Phosphate buffer, pH 7.0, Final activity of each enzyme was measured at 200 U/ml of buffer. The solution was then diluted 1:1 with Gafquat (highly positively charged polymer) formulation and 5 ul of the resulting solution was deposited onto a plastic surface and dried at 30° C. in the presence of silica gel for 2 hours. The process resulted in a dry enzyme bio-surface, with 0.5 U of each enzyme deposited.

Assay Procedure—Utilising 1/80 Sample Dilution

Two approaches were taken, a) reaction of cholesterol sample (plasma) with dried enzymes and Amplex Red in solution, b) reaction of cholesterol sample with both dried enzymes and dried stabilized Amplex Red dye:

(a) Reaction of cholesterol sample (plasma) with dried enzymes and Amplex Red in solution.

Dilution buffer A: 4.16 mM Amplex Red, 10 mM Cholic acid, 0.2% Triton X-100 in Dulbecco phosphate buffered saline pH 7.2.

The sample to be assayed was first diluted 1 part into 80 parts of dilution buffer A, then 50 ul of the diluted sample was used to reconstitute and activate the dried tri-enzyme mix (previously stabilized as described above) in the sample assay chamber.

The cholesterol content was measured by exciting the sample mix at 480 nm and measuring the resulting fluorescence at 600 nm. Cholesterol concentration was determined directly through measurement of the steady state fluorescence after 40 seconds, or Vmax (maximal rate of substrate generation). Each evaluation was made by reference to assay standard data.

(b) Reaction of cholesterol sample (plasma) with both dried enzymes and Amplex Red.

Dilution buffer B: 10 mM Cholic acid, 0.2% Triton X-100 in Dulbecco phosphate buffered saline pH 7.2.

This procedure is similar to the above process. However, in this process the Amplex Red dye was dried in the flow path along with the tri-enzyme mix. Firstly, one defined region of the assay chamber was coated with 0.5 U Cholesterol Esterase (3.1.1.13), 0.5 U Cholesterol Oxidase (1.1.3.6) and 0.5 U Horseradish Peroxidase (1.11.1.7) as described above. A second and separate region of the assay chamber was then coated with 10 μl of Amplex Red/PEG2000 solution and dried at 30-C in the presence of silica gel for 2 hr. The dye coating solution was composed of 5.35 mg/ml Amplex Red, 5% w/v PEG2000 in dimethylsulphoxide (DMSO).

The sample to be assayed was diluted, 1 part into 80 parts of dilution buffer B, and 50 ul of the diluted sample was used to reconstitute and activate the dried Amplex Red dye and tri-enzyme mix in the sample assay chamber.

The cholesterol content was measured by exciting the sample mix at 480 nm and measuring the resulting fluorescence at 600 nm. The cholesterol concentration was again determined directly through either the measurement of Vmax (maximal rate of substrate generation) or so steady state fluorescence after 40 seconds. Each evaluation was made by reference to assay standard data.

Both assays were determined to be capable of determining clinically relevant cholesterol levels of between 2-11 mM.

Assay Procedure—Utilising Undiluted Sample

Neat biological samples were assayed by applying the sample to a borosilicate filter impregnated with anti-HSA antibody located within the consumable device, which serves to filter and direct the sample to an appropriate 200 μm deep read or detection area. Pre-coating of the read area firstly with 400×65 pico-litre droplets of enzyme reagent per mm², followed by 600×65 pico-litre droplets of dye reagent per mm2 and 450×65 pico-litre droplets of inhibitor reagent per mm2 facilitates rapid flow of the sample into the read area. Subsequent excitation of the sample at 480 nm (10 nm band pass) generates fluorescence that can be detected through a 600 nm (10 nm band pass) filter to allow the Total Cholesterol content of the sample to be determined by reference to suitable standard measurements.

Enzyme Reagent: Cholesterol Esterase, Cholesterol Oxidase and Horseradish Peroxidase, each dissolved in a Gafquat stabiliser mix at 200 units per ml.

Detergent solution: 1.63 g Cholic Acid, 10 g Polyethylene glycol 2000, 800 ul Triton X-100 and 253.3 ul of Diethyl Maleate is dissolved in dimethylformamide (DMF) and the final volume adjusted to 40 ml.

Dye Reagent: 5 mg of Ampliflu Red solid added to 480 μl of detergent solution. inhibitor Reagent: 260 mg sodium azide and 912.92 mg potassium phosphate dibasic trihydrate is dissolved in water and the final volume adjusted to 40 ml.

EXAMPLE 2

Total Lipid Assay

The K37 dye was dissolved in DMF to a final concentration of 1.0 mM. Next 5% w/v PEG 2000 was dissolved into the dye solution and 60 nanolitres of the resulting solution was deposited onto a plastic surface and dried by removing the solvent under vacuum for 1 hour at room temperature in the dark.

Assay Procedure—Utilising Diluted Sample

The sample to be assayed (plasma) was first diluted 1 part into 80 parts phosphate buffered saline containing 50 mM Sodium Octanoate, pH 7.4.

5 μl of diluted plasma sample was applied to the dried dye which spontaneously hydrated. The Total lipid content was measured by exciting the sample at 440 nm (10 nm bandpass) and measuring the resulting fluorescence passing through a 495 nm filter (10 nm bandpass). The total lipid content was determined empirically by reference to known standards.

Assay Procedure—Utilising Undiluted Sample

Neat biological samples are assayed by applying the sample to a borosilicate filter impregnated with anti-HSA antibody located within a consumable device, which serves to filter and direct the sample to an appropriate 200 μm deep read area. Pre-coating of the read area with 3000×65 pico-litre droplets of 2 mM K37/5% (w/v) PEG2000 in DMF per mm² facilitates rapid flow of the sample into the read area and spontaneous partitioning of dye into the lipoproteins contained within the sample. Subsequent excitation of the sample at 440 nm (10 nm band pass) generates fluorescence that can be detected through a 495 nm (10 nm band pass) filter to allow the total lipid content of the sample to be determined by reference to suitable standard measurements.

EXAMPLE 3

HDL Cholesterol Assay

Nile Red was dissolved in DMF to a final concentration of 0.5 mM, Next 5% w/v PEG 2000 was dissolved into the dye solution and 60 nanolitres of the resulting solution was deposited onto a plastic surface and dried by removing the solvent under vacuum for 1 hour at room temperature in the dark.

Assay Procedure—Utilising Diluted Sample

The sample to be assayed (plasma) was first diluted 1 part into 80 parts phosphate buffered saline containing 50 mM Sodium Octanoate, pH 7.4.

5 μl of diluted plasma sample was applied to the dried dye which spontaneously hydrated. The HDL cholesterol content was measured by exciting the sample at 580 nm (10 nm bandpass) and measuring the resulting fluorescence passing through a 610 nm filter (10 nm bandpass). HDL cholesterol content was calculated by use of the algorithm described in the main specification. An equivalent assay may also be performed utilising whole, undiluted blood.

Assay Procedure—Utilising Undiluted Sample

Neat biological samples are assayed by applying the sample to a borosilicate filter impregnated with anti-HSA antibody located within a consumable device, which serves to filter and direct the sample to an appropriate 200 μm deep read area. Pre-coating of the read area with 3400×65 pico-iitre droplets of 0.5 mM Nile Red/5% (w/v) PEG2000 in DMF per mm$^2$ facilitates rapid flow of the sample into the read area and spontaneous partitioning of dye into the lipoproteins contained within the sample. Subsequent excitation of the sample at 580 nm (10 nm band pass) generates fluorescence that can be detected through a 610 nm (10 nm band pass) filter to allow the HDL-c content of the sample to be determined by reference to suitable standard measurements.

Manipulating the data from the three tests described in examples 1, 2 and 3 provides the following:
  Measurement of total cholesterol—ie test (1)
  Measurement of total lipid concentration—ie test (2)
  Measurement of HDL cholesterol—ie test (3)
  Calculated value of triglyceride—ie tests (2) less (1)
  Calculated value of VLDL—ie value of triglyceride/2.2
  Calculated value of LDL—ie determined by Friedwald equation

EXAMPLE 4

Use of PEG to Enhance Lateral Fluid Flow in Near Horizontal Capillaries

Glass capillaries 100 mm long and having internal diameters of 2 mm, 1 mm and 0.5 mm were either left untreated, detergent-treated or coated with PEG. The detergent treated capillaries were prepared by washing with a solution of virkon and Triton X100 5% followed by drying. PEG treated capillaries were prepared by flowing 5% (w/v) PEG in chloroform through the capillaries, allowing the surplus to drain followed by drying.

Treated and un-treated capillaries were fixed in a near-horizontal position (about 10° upward flow angle) and the tips of the capillaries were submerged in water. The distance travelled and flow rate of water moving into each capillary was measured:
Untreated Capillaries:
  2 mm—reached 20 mm in ~30 seconds
  1 mm—reached 90 mm in 15 seconds
  0.5 mm—reached end of tube (100 mm) in 18 seconds
Detergent Treated Capillaries
  2 mm—reached 20 mm in ~20 seconds
  1 mm—reached 90 mm in 12 seconds
  0.5 mm—reached end of tube (100 mm) in 15 seconds
PEG-Coated Capillaries:
  2 mm—reached 80 mm in ~20 seconds
  1 mm—reached end in 1-2 seconds
  0.5 mm—reached end of tube (100 mm) in 1-2 seconds This data demonstrates that capillary fluid flow in PEG-coated capillaries is approximately four times faster than in detergent treated capillaries and approximately six times faster than in untreated capillaries.

Capillaries were made hydrophobic by treating with a siliconising agent (dimethyl dichlorosilane) and baking at 120° C. Water did not enter the lumen of these capillaries. Coating the hydrophobic capillaries with PEG (as above) restored the fluid flow conditions comparable to PEG coated capillaries without silation. In some of the experiments where the surface coating of PEG was discontinuous the fluid flow stopped at the break in the PEG coating.

EXPERIMENT 5

Use of PEG to Enhance Fluid Flow in Vertical Capillaries

Capillaries having a length of 100 mm and diameters of 2 mm, 1 mm, or 0.5 mm were treated as described above. The capillaries were fixed in a vertical position and the tips of the capillaries were submerged in water. The Height reached by water in the vertical capillary tubes was measured:
Untreated Tubes:
  2 mm diameter—9 mm
  1 mm diameter—22 mm
  0.5 mm diameter—51 mm
Detergent Treated Tubes
  2 mm diameter—10 mm
  1 mm diameter—22 mm
  0.5 mm diameter—53 mm
PEG-Coated Tubes
  2 mm diameter—11 mm
  1 mm diameter—25 mm
  0.5 mm diameter—54 mm Water did not enter hydrophobic silated capillary tubes at all. By coating the silated capillaries with PEG the capillary flow heights were restored and similar to those of unsilated PEG-coated capillaries.

The theoretical maximum heights at sea level using the equation $h = 2\gamma \cos \theta / \rho g r$, where h is the height (m): $\gamma$ is the surface tension; $\theta$ the contact angle; $\rho$ is the density; g is acceleration due to gravity; and r is the radius of the tube (m) are:
  14 mm at 2 mm ID
  28 mm at 1 mm ID
  56 mm at 0.5 mm ID

EXAMPLE 6

Reproducibility of Transfer and Long-Term Stability

The reproducibility of transfer and long-term stability of hydrophobic molecule (i.e. dye)/amphipathic polymer mixture was measured as follows:

PEG with a molecular weight of 2000 Da was dissolved into a solution of hydrophobic dye (either Nile Red or K37) in dimethylformamide (DMF), at a concentration of 5% w/v, PEG/dye films were made by depositing 25 μl of PEG/dye solution in DMF in a 5 ml glass vial. The solution was spread over the base of the vial and then placed in a vacuum chamber for one hour to evaporate the solvent Reproducibility of transfer was measured by comparing the fluorescence intensity of dye in DMF added to a lipoprotein solution with the fluorescence intensity of an identical lipoprotein solution in which the dye/PEG film was re-dissolved. Reproducibility was calculated by obtaining the Coefficients of variation (CVs) of fluorescence intensities from ten dye/PEG films in lipoprotein solutions.

Stability was evaluated by laying down films for long-term storage, and measuring the fluorescence intensity of these films when re-dissolved in lipoprotein solutions after varying storage times. Films were stored in the dark under a range of conditions: in air with no desiccating agent, in air in the presence of silica gel, and under vacuum in the presence of silica gel. Films were stored under these conditions at temperatures of both 20 and 37° C.

The fluorescence intensities for dyes in lipoprotein solutions dissolved in DMF or in PEG films were determined:

|  | K37 | Nile Red |
|---|---|---|
| From DMF | 268000 | 297000 |
| From PEG film | 269000 | 296000 |

Identical fluorescence intensity readings (within 0.5%) were obtained for PEG films as were obtained when adding dye dissolved in DMF. The reproducibility of fluorescence readings from dye/PEG films with lipoprotein was calculated:

|  | K37 | Nile Red |
|---|---|---|
| Film 1 | 6.23E+05 | 4.27E+05 |
| Film 2 | 6.25E+05 | 4.27E+05 |
| Film 3 | 6.24E+05 | 4.29E+05 |
| Film 4 | 6.25E+05 | 4.26E+05 |
| Film 5 | 6.24E+05 | 4.27E+05 |
| Film 6 | 6.26E+05 | 4.30E+05 |
| Film 7 | 6.23E+05 | 4.30E+05 |
| Film 8 | 6.25E+05 | 4.28E+05 |
| Film 9 | 6.22E+05 | 4.28E+05 |
| Film 10 | 6.22E+05 | 4.26E+05 |
| Mean | 6.24E+05 | 4.28E+05 |
| SD | 1370.32 | 1475.73 |
| CV (%) | 0.22 | 0.34 |

CVs of less than 0.5% were obtained for both dyes.
Stability Measurements

| Time | K37 in DMF 20 C. | K37 in PEG 20 C. in air | K37 in PEG 20 C. in air over silica gel | K37 in PEG 20 C. in vac over silica gel | K37 in PEG 37 C. in air | K37 in PEG 37 C. in air over silica gel | K37 in PEG 37 C. in vac over silica gel |
|---|---|---|---|---|---|---|---|
| Zero | 138630 | 139320 | 137241 | 138624 | 137440 | 138317 | 136942 |
| 1 week | 137500 | 137113 | 137840 | 138801 | 137640 | 136922 | 136817 |
| 4 weeks | 134890 | 134641 | 133980 | 134202 | 135016 | 135412 | 134097 |
| 8 weeks | 135254 | 136021 | 135972 | 136671 | 135926 | 136201 | 135552 |
| % CV | 1.31 | 1.44 | 1.25 | 1.56 | 0.92 | 0.90 | 0.98 |

| Time | NR in DMF 20 C. | NR in PEG 20 C. in air | NR in PEG 20 C. in air over silica gel | NR in PEG 20 C. in vac over silica gel | NR in PEG 37 C. in air | NR in PEG 37 C. in air over silica gel | NR in PEG 37 C. in vac over silica gel |
|---|---|---|---|---|---|---|---|
| Zero | 495197 | 496130 | 494590 | 495760 | 494118 | 494241 | 494829 |
| 1 week | 495002 | 495600 | 494802 | 494400 | 494636 | 493907 | 494621 |
| 4 weeks | 493128 | 492686 | 493440 | 493662 | 494017 | 492506 | 492906 |
| 8 weeks | 493492 | 494620 | 494525 | 493986 | 493920 | 492500 | 493650 |
| % CV | 0.21 | 0.31 | 0.12 | 0.19 | 0.06 | 0.19 | 0.18 |

Conclusions:

(1) Dyes incorporated into PEG films fully re-dissolve when reconstituted with aqueous solutions, and give the same fluorescence intensities as dyes added in organic solvents.

(2) The dye/PEG films are reproducible and films made up in the same way result in the same fluorescence intensity.

(3) The dye/PEG films are stable for at least 52 weeks when stored under the harshest storage conditions tested (37° C., no desiccant).

EXAMPLE 7

Comparison of Amphipathic/Non-Ionic Polymers

Borosilicate capillaries (100 mm long, 1 mm ID from Composite Metal Services Ltd—CV1012) were coated by drawing up 7 mm of a 5% polymer solution in various solvents and rocked until dry. The solvent used was dependent on solubility with chloroform favoured because of its high evaporation rate.

Experiments on the coated capillaries were performed in triplicate and an uncoated capillary was run: each time as a reference. The 4 capillaries were held vertical on a lined reference card by 2 slots cut into the card for each capillary. The ends of the capillaries extended exactly 7 mm past the bottom of the card.

The experiment was videoed using a Sunkwang High Resolution Low Lux Color Camera connected to a Winnov 500050G V1000+CV PC card and the program Videum Capture was used to capture and analyse the data. The frame rate was set at 5 frames per second (to avoid dropped frames) unless otherwise stated. The flow liquid (10-4M Rose Bengal in water) was contained in a flat bottomed watch glass and the card simply lowered end-on until the bottom of the card came to rest on the walls of the watch glass. Capillaries were submerged in the flow liquid to a depth of 2 mm. This produced a gap of 5 mm to the bottom of the card, 9 mm from the bottom of the card to the first line and a further 6 mm to the second line up the card. Flow rates were calculated by counting how many frames elapsed for the 9 mm of travel between the bottom of the card and the first line,

TABLE 1

Performance of polymer coatings/solvent systems in water column height and capillary flow rate.

| Coating | Solvent | Average water column height mm | STDEV on column height | Average flow rate mm/s | STDEV on average flow rate mm/s | Fastest rate mm/s |
|---|---|---|---|---|---|---|
| PEG2000 | Chloroform | 17.8 | 0.76 | 21.9 | 3.3 | 25.7 |
| PEG2000 | DMF | 19.8 | 1.89 | 27.6 | 28.1 | 60 |
| PEG2000 | Water | 13.5 | 5.77 | 29.7 | 37.2 | 72 |
| PEG6000 | Chloroform | 19.3 | 0.76 | 21.5 | 4.8 | 25.7 |
| PEG12,000 | Chloroform | 16.5 | 0.87 | 7.6 | 3.3 | 9.5 |
| PEG20,000 | Chloroform | 15.3 | 1.04 | 3.2 | 1.6 | 4.9 |
| Triton X100 | Water | 14.2 | 1.04 | 7.9 | 2.2 | 10 |
| Carboxymethyl cellulose | Water | 18.0 | * | 180 | * | 180 |
| 0,0'-Bis(2-aminoethyl) polyethylene glycol 2000 | Chloroform | 17.0 | 3.5 | 38.8(52.5) | 25.0(10.6) | 60 |
| PEG methyl ether 5000 | Chloroform | 17.8 | 1.26 | 2.4 | 0.2 | 2.6 |

\* = a result from a single capillary ( ) = a result from 2 out of 3 capillaries as capillary had a column height below the first line of the card and was therefore estimated.

Figure 7:
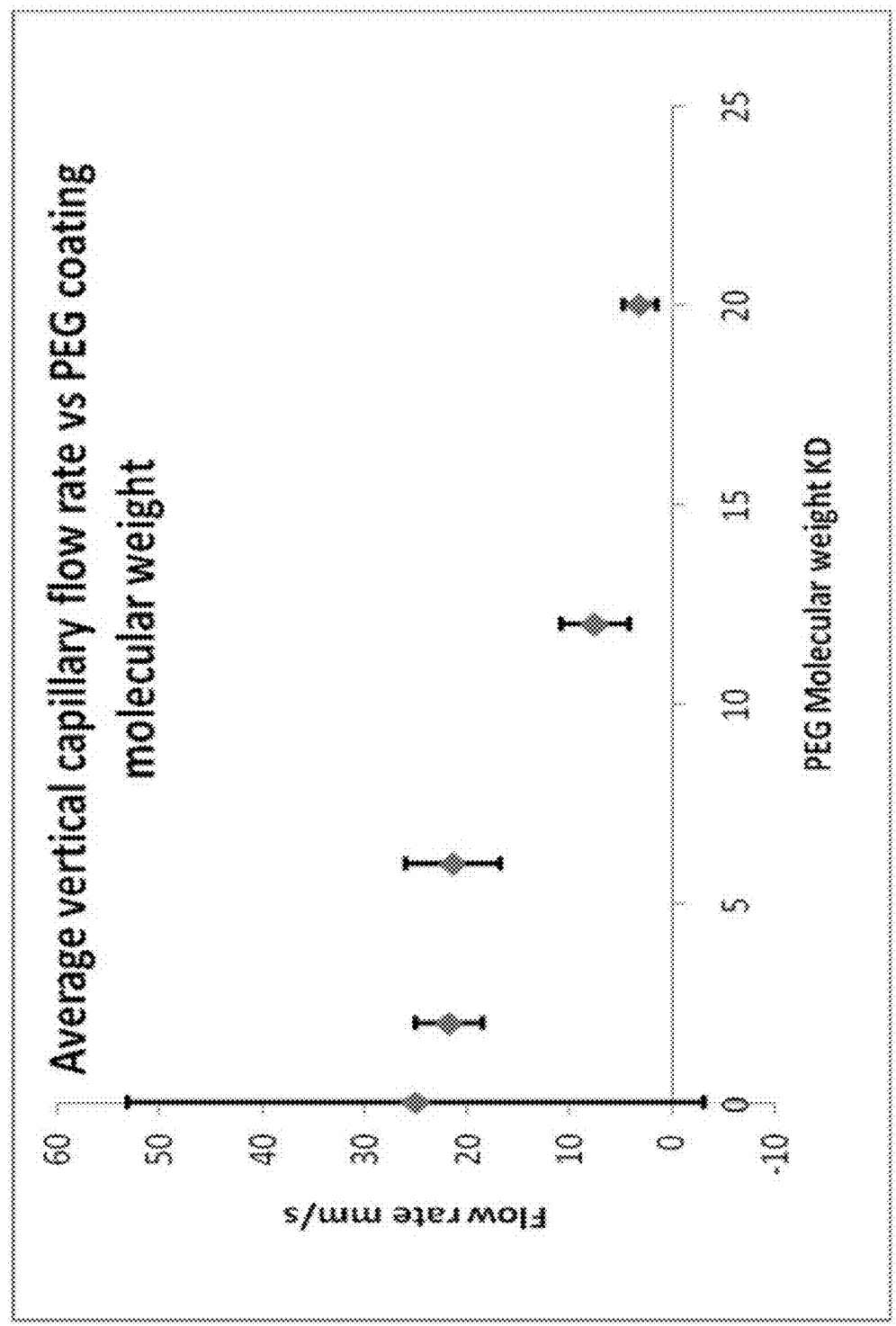
FIG. 7 illustrates the effect of molecular weight of PEG on vertical flow rate.

FIG. 7 illustrates the effect of molecular weight of PEG on vertical flow rate.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. An assay device comprising:
   a first region;
   a second region; and
   at least one fluid flow pathway operatively connecting the first region to the second region and configured to transfer a fluid sample from the first region to the second region via capillary flow;
   wherein the fluid flow pathway comprises two substantially flat opposing surfaces with a gap between, wherein the two surfaces are formed of a hydrophobic plastic and wherein at least one of the two surfaces includes a printed amphipathic polymer, the gap between the opposing surfaces defining a volume through which the fluid sample is transferred from the first region via the fluid flow pathway to the second region, and wherein the two substantially flat opposing surfaces of the fluid flow pathway exhibit different hydrophobicity/hydrophilicity at least partly as a result of the printed amphipathic polymer, thereby disrupting capillary laminar flow while enhancing capillary flow rate of the fluid sample in the volume travelling between, and in simultaneous contact with, the two substantially flat opposing surfaces; and wherein the fluid flow pathway further comprises at least one reagent.

2. The assay device of claim 1, wherein one of the two substantially opposing surfaces defines an open capillary channel having a cross sectional geometry sufficient to create an open channel configured to form a closed capillary channel with the second of the two substantially opposing surfaces.

3. The assay device of claim 1, wherein spacer elements are configured to hold the two substantially opposing surfaces some distance apart to create a capillary channel between said surfaces.

4. The assay device according to claim 1, further comprising an application area in fluid communication with the first region of the device for introduction of a fluid sample.

5. The assay device as claimed in claim 4, comprising an aperture in one of the two substantially opposing surfaces for introduction of a fluid sample to the application area.

6. The assay device as claimed in claim 4, further comprising at least one vent port located in the second region of the device.

7. The assay device as claimed in claim 4, further comprising a flow stop junction between the first and second regions of the device configured to halt or pause capillary fluid flow of a fluid travelling between the two substantially opposing surfaces.

8. The assay device as claimed in claim 7, wherein the device further comprises a filter membrane disposed between the application area and the at least one fluid flow pathway.

9. The assay device as claimed in claim 1, wherein the at least one reagent is selected from the group consisting of dyes, probes, enzymes, and ligand binding inhibitors.

10. The assay device as claimed in claim 9, wherein the fluid flow pathway comprises one or more dyes or probes selected from the group consisting of Amplex Red, K37 and Nile Red.

11. The assay device as claimed in claim 9, wherein the fluid flow pathway comprises one or more enzymes selected from the group consisting of Cholesterol esterase, Cholesterol oxidase and Horseradish peroxidise.

12. The assay device as claimed in claim 9, wherein the fluid flow pathway comprises one or more ligand binding inhibitors selected from the group consisting of alkali metal octanoate and octanoic acid.

13. The assay device as claimed in claim 9, further comprising at least one detection zone configured for measurement of the result and/or progress of a reaction between at least a part of a fluid sample and the at least one reagent.

14. The assay device as claimed in claim 13, which comprises at least three fluid flow pathways and at least three detection zones wherein, a first flow pathway is in fluid communication with the application area and a first detection zone, a second fluid flow pathway is in fluid communication with the application area and a second detection zone and a third fluid flow pathway is in fluid communication with the application area and a third detection zone.

15. The assay device as claimed in claim 14, wherein the first fluid flow pathway comprises Amplex Red, the second fluid flow pathway comprises K37 and the third fluid flow pathway comprises Nile Red.

16. The assay device as claimed in claim 15, wherein the first fluid flow pathway further comprises cholesterol esterase, cholesterol oxidase and horseradish peroxidise.

17. A kit of components comprising at least one assay device as claimed in claim 1, and further comprising one or more of (i) a means for sterilizing a patient's skin; (ii) skin penetrating means; (iii) gauze; (iv) adhesive plasters; (v) instructional leaflets providing details on use of the device; (vi) disposable gloves and (vii) an assay reader.

18. A method comprising:
providing an assay device comprising
a first region;
a second region; and
at least one fluid flow pathway operatively connecting the first region to the second region and configured to transfer a fluid sample from the first region to the second region via capillary flow;
wherein the fluid flow pathway comprises two substantially flat opposing surfaces with a gap between, where the two opposing surfaces are hydrophobic plastics and one of the two surfaces includes a printed amphipathic polymer, the gap between the opposing surfaces defining a volume through which the fluid sample is transferred from the first region via the fluid flow pathway to the second region, and wherein the two substantially flat opposing surfaces of the fluid flow pathway exhibit different hydrophobicity/hydrophilicity at least partly as a result of the printed amphipathic polymer, thereby disrupting capillary laminar flow while enhancing capillary flow rate of the fluid sample in the volume travelling between, and in simultaneous contact with, the two substantially flat opposing surfaces,
and wherein the at least one fluid flow pathway comprises at least one reagent, and the disruption in the capillary laminar flow increases mixing between the fluid sample and the at least one reagent, and wherein the assay device further comprises an application area in fluid communication with the first region of the device for introduction of a fluid sample, and at least one detection zone configured for measurement of the result and/or progress of a reaction between at least a part of a fluid sample and the at least one reagent;
introducing a fluid sample into the application area to allow a reaction to occur between the at least a part of the fluid sample and the at least one reagent in the fluid flow pathway; and
detecting the result or the progress of the reaction via the detection zone.

* * * * *